US008105700B2

(12) United States Patent
Thompson et al.

(10) Patent No.: US 8,105,700 B2
(45) Date of Patent: Jan. 31, 2012

(54) MATERIALS AND STRUCTURES FOR ENHANCING THE PERFORMANCE OF ORGANIC LIGHT EMITTING DEVICES

(75) Inventors: Mark E. Thompson, Anaheim Hills, CA (US); Raymond Kwong, Plainsboro, NJ (US); Yeh-Jiun Tung, Princeton, NJ (US); Jason Brooks, Lambertville, NJ (US)

(73) Assignees: Universal Display Corporation, Ewing, NJ (US); The University of Southern California, Los Angeles, CA (US)

( * ) Notice: Subject to any disclaimer, the term of this patent is extended or adjusted under 35 U.S.C. 154(b) by 1001 days.

(21) Appl. No.: 11/974,020

(22) Filed: Oct. 10, 2007

(65) Prior Publication Data
US 2008/0309222 A1 Dec. 18, 2008

Related U.S. Application Data

(60) Division of application No. 10/785,287, filed on Feb. 23, 2004, now abandoned, which is a continuation-in-part of application No. 10/626,579, filed on Jul. 25, 2003, now Pat. No. 7,018,723.

(51) Int. Cl.
H01L 51/54 (2006.01)
(52) U.S. Cl. ........ 428/690; 428/917; 313/504; 313/506; 257/E51.049
(58) Field of Classification Search .................. None
See application file for complete search history.

(56) References Cited

U.S. PATENT DOCUMENTS

| | | | |
|---|---|---|---|
| 4,769,292 | A | 9/1988 | Tang et al. |
| 5,077,142 | A | 12/1991 | Sakon et al. |
| 5,247,190 | A | 9/1993 | Friend et al. |
| 5,281,489 | A | 1/1994 | Mori et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 5,989,737 | A | 11/1999 | Xie et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,150,042 | A | 11/2000 | Tamano et al. |
| 6,245,449 | B1 | 6/2001 | Tamano et al. |
| 6,294,398 | B1 | 9/2001 | Kim et al. |
| 6,303,238 | B1 | 10/2001 | Thompson et al. |
| 6,310,360 | B1 | 10/2001 | Forrest et al. |
| 6,337,102 | B1 | 1/2002 | Forrest et al. |
| 6,468,819 | B1 | 10/2002 | Kim et al. |
| 6,492,041 | B2 | 12/2002 | Ishiskawa et al. |
| 2002/0034656 | A1 | 3/2002 | Thompson et al. |
| 2002/0038860 | A1 | 4/2002 | Tsuboyama et al. |
| 2002/0064679 | A1 | 5/2002 | Ishiskawa et al. |
| 2002/0177009 | A1 | 11/2002 | Suzuki et al. |
| 2002/0182441 | A1 | 12/2002 | Lamansky et al. |
| 2003/0039858 | A1 | 2/2003 | Igarashi et al. |
| 2003/0072964 | A1 | 4/2003 | Kwong et al. |
| 2003/0230980 | A1 | 12/2003 | Forrest et al. |
| 2004/0076853 | A1 | 4/2004 | Jarikov |
| 2004/0155238 | A1 | 8/2004 | Thompson et al. |
| 2006/0134456 | A1 | 6/2006 | Ikeda et al. |

FOREIGN PATENT DOCUMENTS

| | | |
|---|---|---|
| JP | 1192420 A | 4/1999 |
| WO | 99/65961 | 12/1999 |
| WO | WO 02/074015 | 9/2002 |
| WO | WO 03/007658 | 1/2003 |

OTHER PUBLICATIONS

Bacher et al., "Triphenylenes: a new class of hole transport material in organic light emitting diodes," SPIE, vol. 3148, pp. 313-320 (1997).
Vadim I. Adamovich et al., "New Charge-Carrier Blocking Materials for High Efficiency OLEDs," MRS Spring Meeting, Apr. 2002, San Francisco, CA.
Vadim I. Adamovich et al., "New charge-carrier blocking materials for high efficiency OLEDs," Organic Electronics, vol. 4, p. 77-87 (2003).
Kenji Okumoto et al., "New Class of Hole-Blocking Amorphous Molecular Materials and their Application in Blue-Violet-Emitting Fluorescent and Green-Emitting Phosphorescent Organic Electroluminescent Devices," Chem. Mater., vol. 15, pp. 699-707 (2003).
Baldo et al., "Highly Efficient Phosphorescent Emission from Organic Electroluminescent Devices," Nature, vol. 395, 151-154, 1998.
Baldo et al., "Very High-Efficiency Green Organic Light-Emitting Devices Based on Electrophosphorescence," Appl. Phys. Lett., vol. 75, No. 1, 4-6 (1999)
Adachi et al., "Nearly 100% Internal Phosphorescent Efficiency in an Organic Light Emitting Device," J. Appl. Phys., 90, 5048 (2001).
Wong et al., "Ter(9,9-diarylfluorene)s: Highly Efficient Blue Emitter with Promising Electrochemical and Thermal Stability," J. Am. Chem. Soc., 124, pp. 11576-11577 (2002).
Lu, et al., U.S. Appl. No, 09/931,948, filed Aug. 20, 2001, entitled "Transparent electrodes". (pub'd Sep. 2004 as 2004/0174116 A1).
Shtein, et al., U.S. Appl. No. 10/233,470, filed Sep. 4, 2002, entitled "Process and apparatus for organic vapor jet deposition". (pub'd Sep. 2008 as 2008/0233287 A1).
M. Kinoshita, et al., "A Novel Family of Boron-Containing Hole-Blocking Amorphous Molecular Materials for Blue- and Blue-Violet-Emitting Organic Electroluminescent Devices", Adv. Funct. Mater., 10, No. 11-12, pp. 780-786, Dec. 2002.

(Continued)

Primary Examiner — Marie R. Yamnitzky
(74) Attorney, Agent, or Firm — Kenyon & Kenyon LLP

(57) ABSTRACT

A device is provided, having an anode, a cathode, and two adjacent organic layers disposed between the anode and the cathode. One organic layer is a phosphorescent emissive material. The other organic layer may comprise an aromatic hydrocarbon material, comprising an aromatic non-heterocyclic hydrocarbon core optionally substituted, and wherein the substituents are the same or different, and each is selected from the group consisting of alkyl, alkenyl, alkynyl, aryl, heteroalkyl, substituted aryl, substituted heteroaryl and heterocyclic groups. The second organic layer may comprise a material having a molecular dipole moment less than about 2.0 debyes, such that the device has an unmodified external quantum efficiency of at least about 3% and a lifetime of at least about 1000 hours at an initial luminance of about 100 to about 1000 cd m$^2$.

9 Claims, 22 Drawing Sheets

OTHER PUBLICATIONS

C. Adachi, et al., "High-efficiency organic electrophosphorescent devices with tris(2-phenylpyridine)iridium doped into electron-transporting materials", Applied Physics Letters, vol. 77, No. 6, pp. 904-906, Aug. 7, 2000.

C. Lee, et al., "Polymer phosphorescent light-emitting devices doped with tris(2-phenylpyridine) iridium as a triplet emitter", Applied Physics Letters, vol. 77, No. 15, pp. 2280-2282, Oct. 9, 2000.

Y. Wang, et al., "Highly efficient electroluminescent materials based on fluorinated organometallic iridium compounds", Applied Physics Letters, vol. 79, No. 4, pp. 449-451, Jul. 23, 2001.

R. Kwong, et al., "High operational stability of electrophosphorescent devices", Applied Physics Letters, vol. 81, No. 1, pp. 162-164, Jul. 1, 2002.

Boden et al., "Syntheses of new "large core" discogens based on the triphenylene, azatriphenylene and hexabenztrinaphthylene nuclei", Liquid Crystals 28(1):pp. 139-144 (2001).

Wegewijs et al., "Charge-carrier mobilities in binary mixtures of discotic triphenylene derivatives as a function of temperature", Physical Review B., vol. 65, pp. 245112-1-245112-8 (2002).

MATERIALS AND STRUCTURES FOR ENHANCING THE PERFORMANCE OF ORGANIC LIGHT EMITTING DEVICES

This application is a division of U.S. patent application Ser. No. 10/785,287, filed Feb. 23, 2004, now abandoned, which is a continuation-in-part of U.S. application Ser. No. 10/626,579, filed Jul. 25, 2003, now U.S. Pat. No. 7,018,723, which are incorporated herein by reference in their entirety.

GOVERNMENT RIGHTS

Using the specific language required by 37 C.F.R. §401.14 (f)(4): This invention was made with government support under Contract No. MDA-972-01-1-0032 awarded by the Defense Advanced Research Project Agency (DARPA). The government has certain rights in this invention.

RESEARCH AGREEMENTS

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to efficient organic light emitting devices (OLEDs), and more specifically to phosphorescent aromatic organic non-heterocyclic hydrocarbon materials with improved stability and efficiency used in such devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic optoelectronic device. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

SUMMARY OF THE INVENTION

A device is provided, having an anode, a cathode, and a first organic layer disposed between the anode and the cathode. The first organic layer comprises a material that produces phosphorescent emission when a voltage is applied between the anode and the cathode. A second organic layer disposed between the first organic layer and the cathode is also provided. The second organic layer is in direct contact with the first organic layer. The second organic layer may comprise an aromatic non-heterocyclic hydrocarbon compound. Particularly suitable aromatic hydrocarbon materials include materials having the following structures:

I
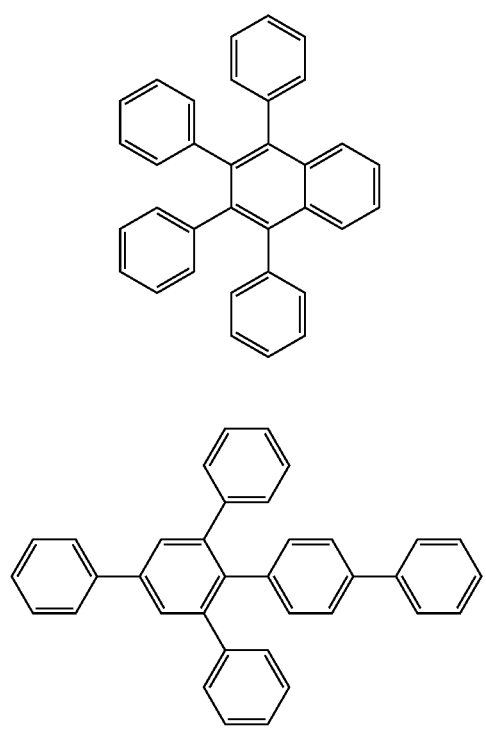
II
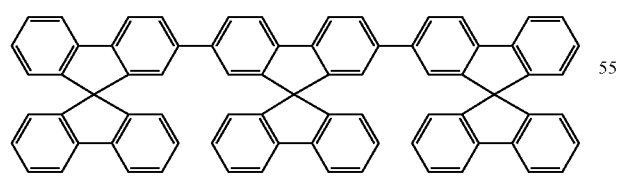
III
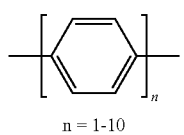
VI
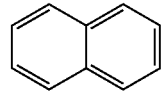
VII
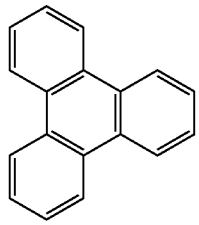
VIII
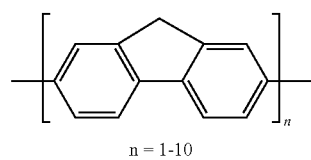
n = 1-10
IX
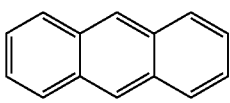
X
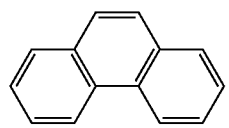
XI
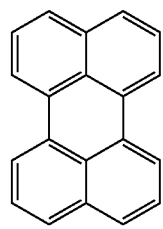
XII
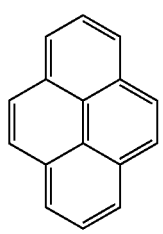
Each aromatic ring may optionally be substituted. Particularly suitable aromatic non-heterocyclic hydrocarbon materials with substituted rings include materials having the following structures:

XIII 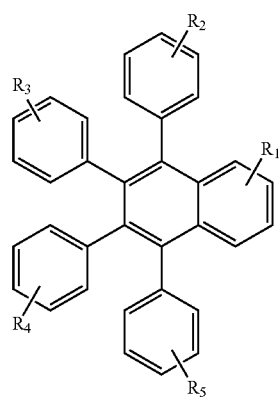 XIV 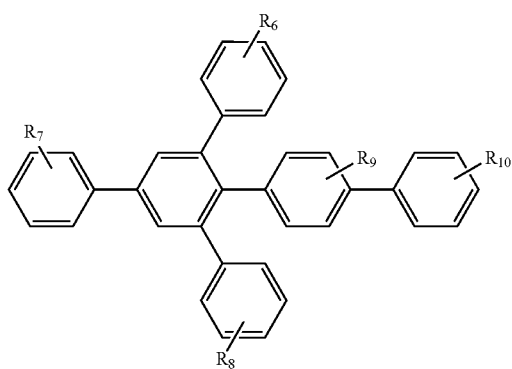
XV 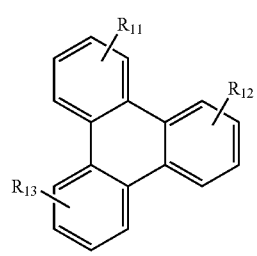
XVI 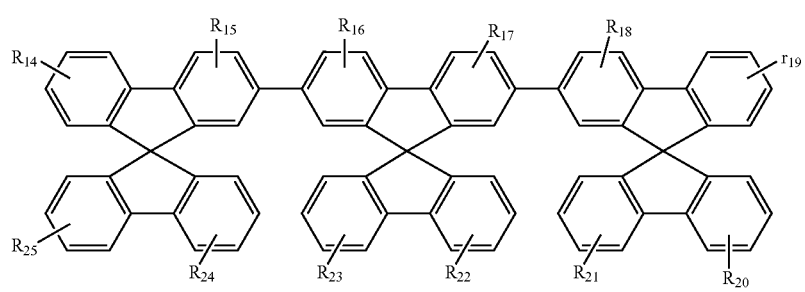
XVII 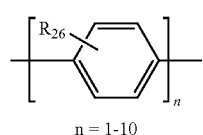 XVIII 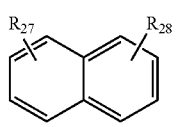
XIX 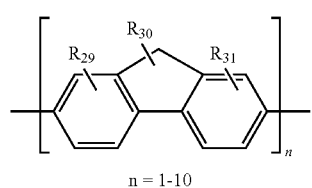 XX 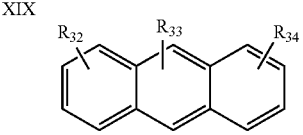
XXI 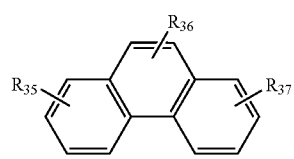 XXII 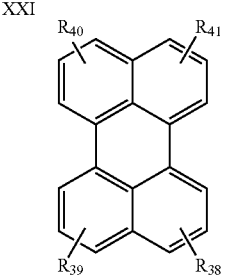

-continued

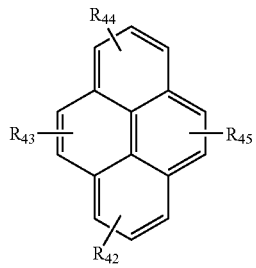

XXIII wherein:

$R_1$-$R_{10}$ each represent no substitution, mono-, di-, or tri-substitution, and wherein $R_1$-$R_{10}$ are the same or different substituents, and each is selected from the group consisting of alkyl, alkenyl, aryl, heteroalkyl and substituted aryl groups; $R_{11}$-$R_{13}$, $R_{15}$-$R_{18}$, $R_{29}$-$R_{45}$ each represents no substitution, mono-, di-, or tri-substitution, and wherein $R_{11}$-$R_{13}$, $R_{15}$-$R_{18}$, $R_{29}$-$R_{45}$ are the same or different substituents, and each is selected from the group consisting of alkyl, alkenyl, alkynyl, aryl, heteroalkyl, and substituted aryl; $R_{14}$, $R_{19}$, and $R_{20}$-$R_{28}$ each represents no substitution, mono-, di-, or tri- or tetra-substitution and $R_{14}$, $R_{19}$, and $R_{20}$-$R_{28}$ are the same or different substituents, and each is selected from the group consisting of alkyl, alkenyl, alkynyl, aryl, heteroalkyl and substituted aryl, and substituent R of each hydrocarbon structure may be linked together to form cyclic substituents such as cycloalkyl or aromatic non-heterocyclic rings.

The second organic layer may comprise a material having a molecular dipole moment less than about 2.0 debyes, such that the device has an unmodified external quantum efficiency of at least about 3%, and a lifetime of at least about 1000 hours at an initial luminance of about 100 to about 1000 cd/m². The second organic layer may be in direct contact with the cathode, or there may be a separate organic layer between the second organic layer and the cathode. Other aromatic hydrocarbon materials may be used.

DETAILED DESCRIPTION

Figure 1:
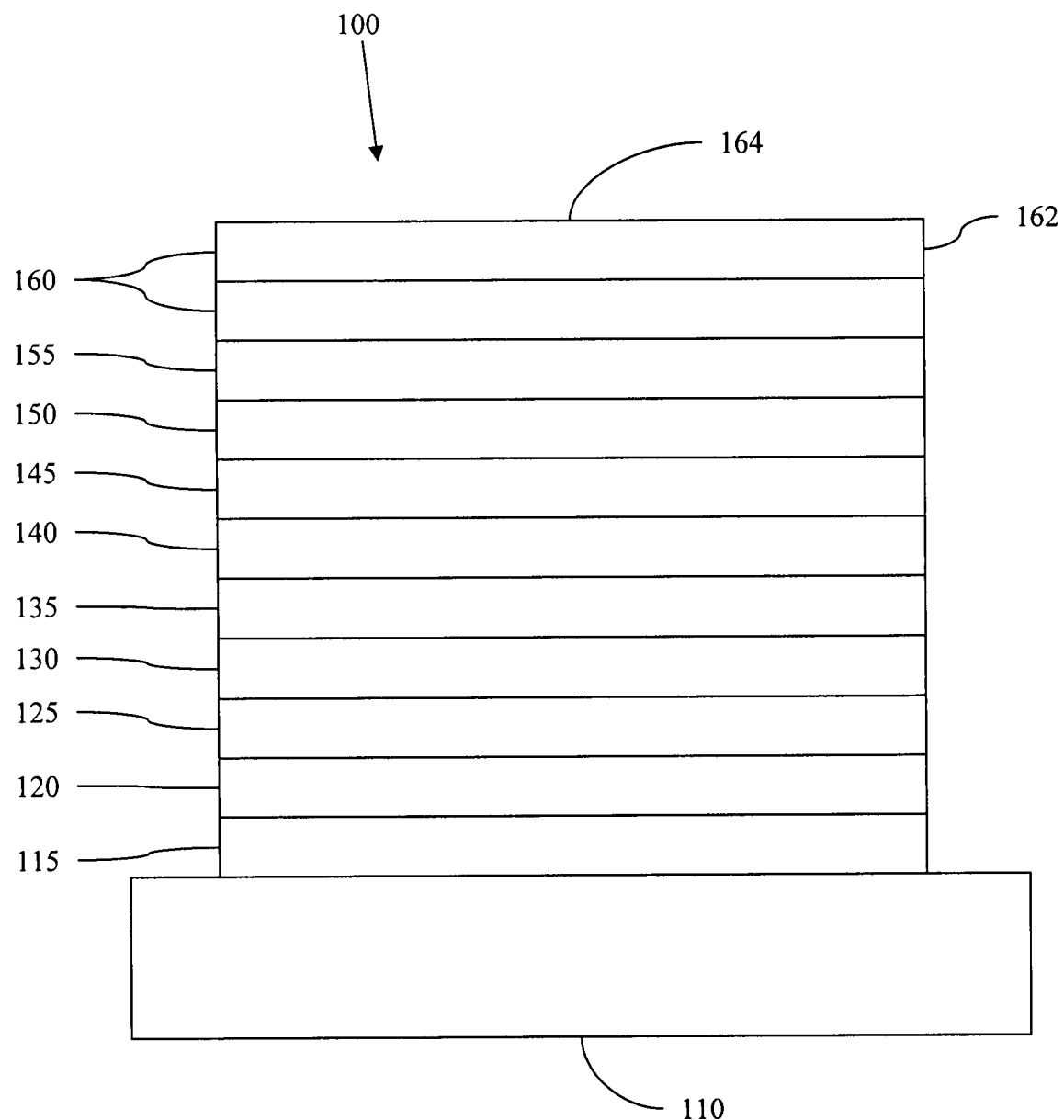
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. However, as demonstrated by Baldo, this problem may be addressed by selecting phosphorescent compounds that do phosphoresce at room temperature. Representative emissive layers include doped or un-doped phosphorescent organo-metallic materials such as disclosed in U.S. Pat. Nos. 6,303,238 and 6,310,360; U.S. Patent Application Publication Nos. 2002-0034656; 2002-0182441; and 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent, or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 125 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. patent application Ser. No. 10/173,682 to Forrest et al. (published as US 2003/0230980), which is incorporated by reference in its entirety. Other hole transport layer materials and structures may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP, and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. Other emissive layer materials and structures may be used.

Electron transport layer 140 may include a material capable of transporting electrons. Electron transport layer 140 may be intrinsic (undoped), or doped. Doping may be used to enhance conductivity. Alq$_3$ is an example of an intrinsic electron transport layer material. An example of an n-doped electron transport layer material is BPhen doped with Li at a molar ratio of 1:1, as disclosed in U.S. patent application Ser. No. 10/173,682 to Forrest et al. (published as US 2003/0230980), which is incorporated by reference in its entirety. Other electron transport layer materials and structures may be used.

The charge carrying component of the electron transport layer may be selected such that electrons can be efficiently injected from the cathode into the LUMO (Lowest Unoccupied Molecular Orbital) level of the electron transport layer. The "charge carrying component" is the material responsible for the LUMO that actually transports electrons. This component may be the base material, or it may be a dopant. The LUMO level of an organic material may be generally characterized by the electron affinity of that material while relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, to achieve high electron injection efficiency, the work function of the cathode material is preferably not greater than the electron affinity of the charge carrying component of the electron transport layer by more than about 0.75 eV, more preferably, by not more than about 0.5 eV. Most preferably, the electron affinity of the charge carrying component of the electron transport layer is greater than the work function of the cathode material. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and U.S. patent application Ser. No. 10/173,682 to Forrest et al. (published as US 2003/0230980), which are incorporated by reference in their entireties. The conventional "blocking layer" is generally believed to reduce the number of charge carriers and/or excitons that leave the emissive layer by presenting an energy barrier that the charge carrier or exciton has difficulty surmounting. For example hole transport is generally thought to be related to the Highest Occupied. Molecular Orbital (HOMO) of an organic semiconductor. A "hole blocking" material may therefore be generally considered as a material that has a HOMO energy level significantly less than that of the material from which the holes are being blocked. A first HOMO energy level is considered "less than" a second HOMO energy level if it is lower on a conventional energy level diagram, which means that the first HOMO energy level would have a value that is more negative than the second HOMO energy level. For example, Ir(ppy)$_3$ has a HOMO energy level of −4.85 eV (data is based on the density function calculation using the B3LYP 6-31G* basis set, Spartan 02 software package, with the pseudopetential option for materials containing heavy metals such as Ir(ppy)$_3$). Boron 1 has a HOMO energy level of −6.49 eV, which is 1.64 eV less than that of Ir(ppy)$_3$, making it an excellent hole blocker. ZrQ$_4$ has a HOMO energy level of −5.00, only 0.15 eV less than that of Ir(ppy)$_3$, such that little or no hole blocking is expected. mer-GaQ$_3$ has a HOMO energy level of −4.63 eV, which is greater than that of Ir(ppy)$_3$, such that no hole blocking at all is expected. If the emissive layer includes different materials with different energy levels, the effectiveness of these various materials as hole blocking layers may be different, because it is the difference in HOMO energy levels between the blocking layer and the blocked layer that is significant, not the absolute HOMO energy level. But, the absolute HOMO level may be useful in determining whether a compound will be a good hole blocker for particular emissive layers. For example, a material having a HOMO energy level of about −5.15 eV or less may be considered a reasonable hole blocking material for Ir(ppy)$_3$, which is a representative emissive material. Generally, a layer having a HOMO energy level that is at least 0.25 eV less than that of an adjacent layer may be considered as having some hole blocking properties. An energy level difference of at least 0.3 eV is preferred, and an energy level difference of at least 0.7 eV is more preferred. Similarly, the energy of an exciton is generally believed to be related to the band gap of a material. An "exciton blocking" material may generally be thought of as a material having a band gap significantly larger than the material from which excitons are being blocked. For example, a material having a band gap that is about 0.1 eV or more, larger than that of an adjacent material, may be considered a good exciton blocking material.

As used herein, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. In addition, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, for example, hole injection layer 120 may be any layer comprising a material that improves the injection of holes from anode 115 into hole transport layer 125. Exemplary materials include CuPc. In device 100, electron injection layer 150 may be any layer comprising a material that facilitates or enhances the injection of electrons into electron transport layer 145. Exemplary materials include LiF/Al. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., now U.S. Pat. No. 7,071,615, which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., now U.S. Pat. No. 7,071,615, which is incorporated by reference in its entirety.

Figure 2:
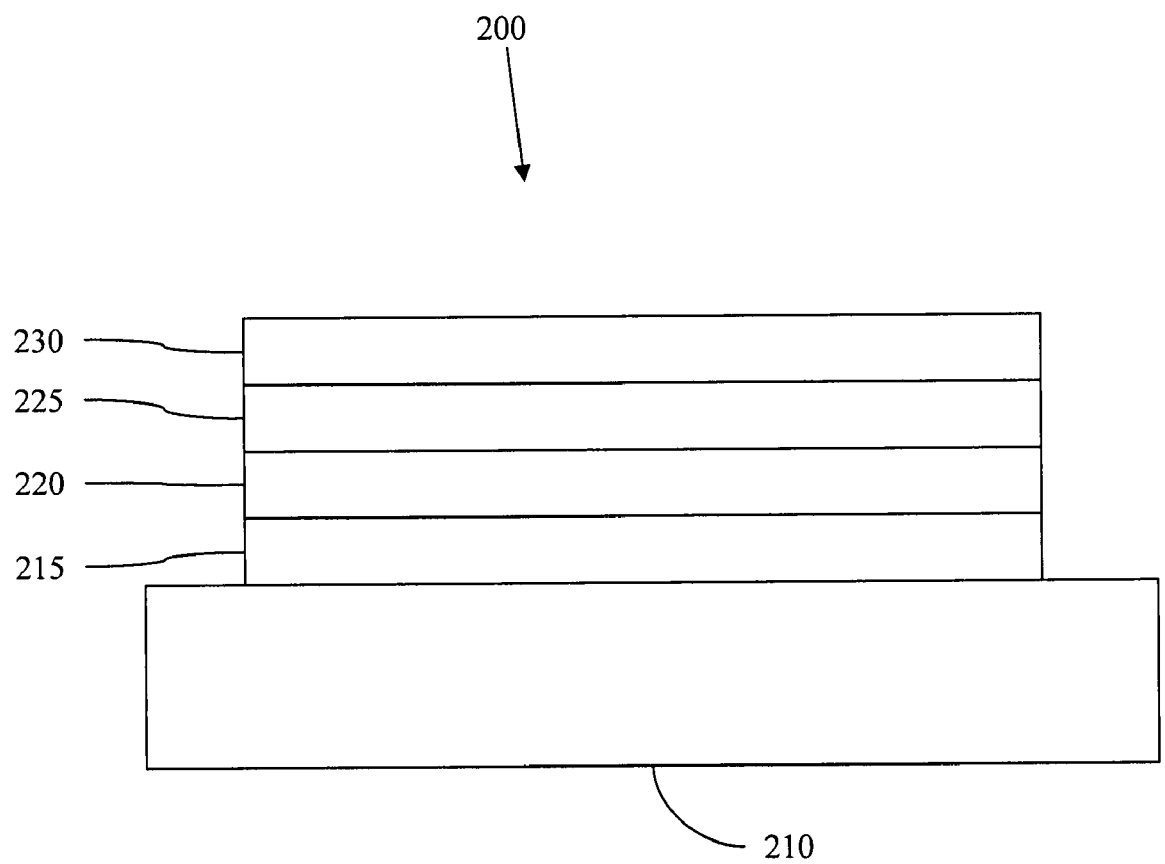
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. In addition, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18° C. to 30° C., and more preferably at room temperature (20°-25° C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

As used herein, "solution processible" means capable of being dissolved, dispersed, or transported in and/or deposited from a liquid medium, either in solution or suspension form.

In an embodiment of the invention, an organic enhancement layer is provided that is disposed between the cathode and the first organic emissive layer of an organic light emitting device. The organic enhancement layer is in direct contact with the emissive layer. In one embodiment, the organic enhancement layer may also be in direct contact with the cathode.

Figure 3:
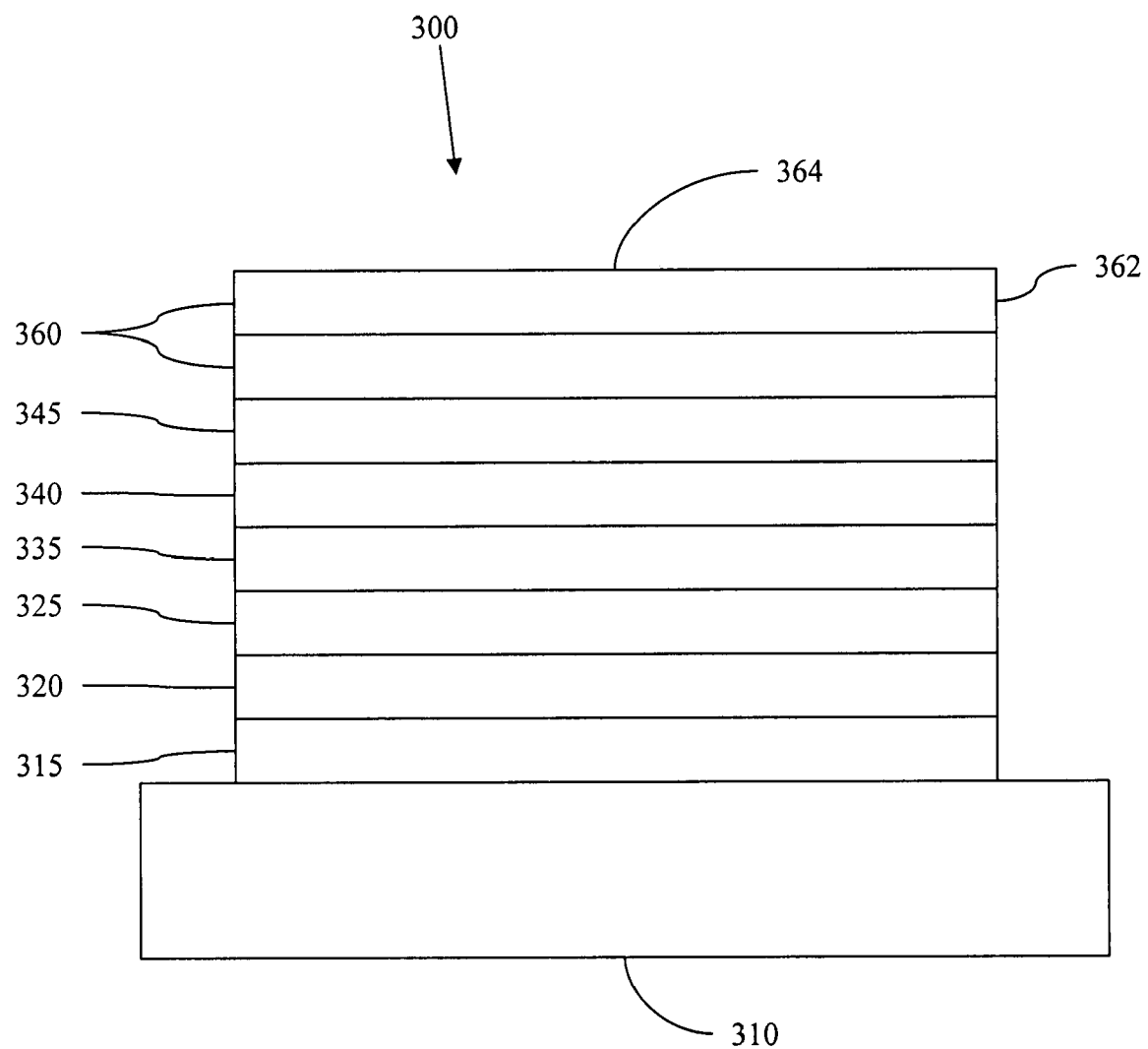
FIG. 3 shows a device having an organic enhancement layer that is not in direct contact with the cathode.
Figure 4:
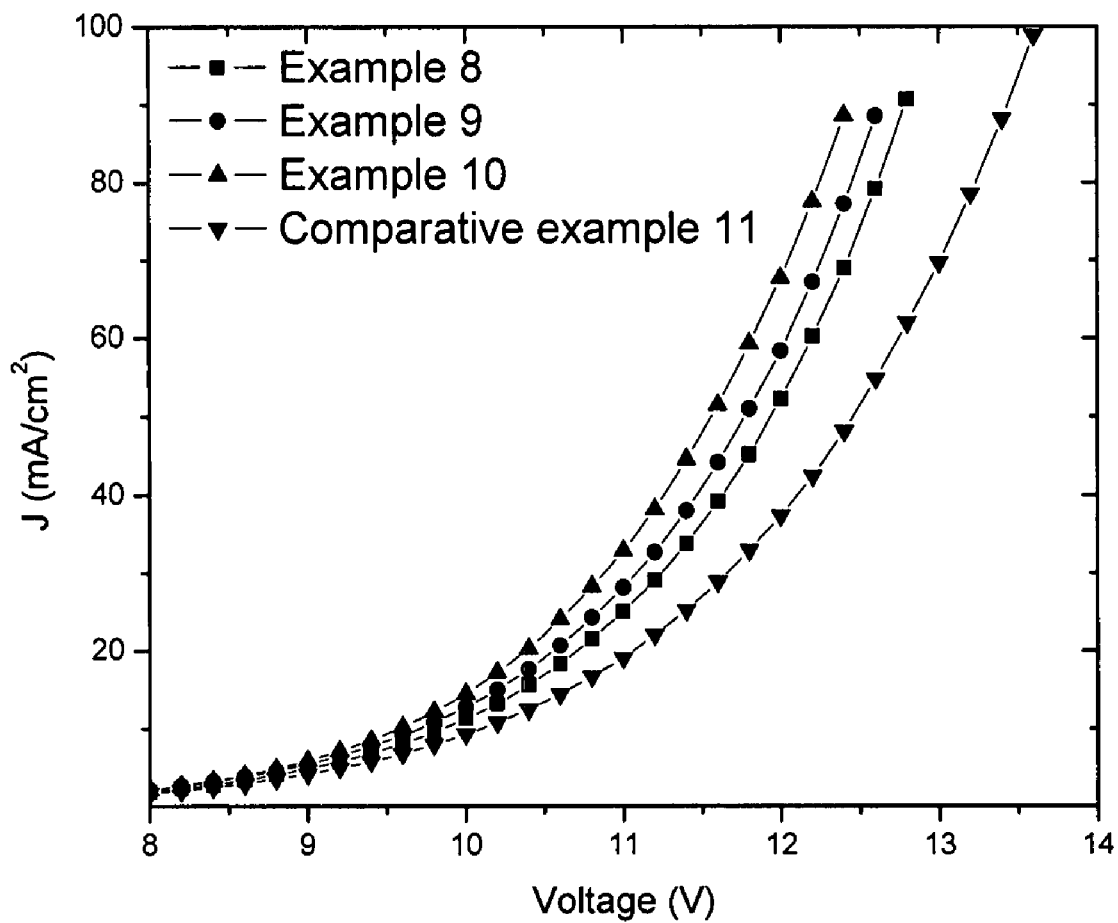
FIG. 4 shows current-voltage characteristics for examples 8-10 and comparative example 11.

FIG. 3 shows a device 300 having an organic enhancement layer that is not in direct contact with the cathode, because there is a separate electron transport layer. Device 300 includes a substrate 310, an anode 315, a hole injection layer 320, a hole transport layer 325, an organic emissive layer 335, an organic enhancement layer 340, an electron transport layer 345, and a cathode 360. Cathode 360 includes a first conductive layer 362 and a second conductive layer 364. Similarly named layers operate analogously to substrate 110, anode 115, hole injection layer 120, hole transport layer 125, emissive layer 135, electron transport layer 145, and cathode 160 of FIG. 1.

The organic enhancement layer 340 may improve device performance. The organic enhancement layer 340 is not necessarily a hole blocking layer, and may have a HOMO energy level that is greater than that of emissive layer 335, not more than 0.3 eV less than that of emissive layer 335, or not more than 0.7 eV less than that of emissive layer 335. Where the organic emissive layer includes multiple materials, such as a host and a dopant, the HOMO energy level of the emissive layer is considered to be that of the component that transports holes, which is generally the component having the highest HOMO energy level, provided that the component is present in an appreciable amount, for example about 3% or higher. For example, in a device having an emissive layer comprising CBP doped with Ir(ppy)$_3$, the HOMO level of Ir(ppy)$_3$, which is −4.85 eV, is the HOMO level relevant to charge transport, because it is higher than the HOMO level of CBP, −5.32 eV. Without being bound to any particular theory of how the invention works, it is believed that the organic enhancement layer 340 improves device performance by improving electron injection into emissive layer 335. Factors that may assist in achieving these properties include the use of a material in organic enhancement layer 340 having a low molecular dipole moment. In some embodiments, organic enhancement layer 340 may act as a hole blocking layer, which may further enhance device performance, but this is not necessary.

In one embodiment of the invention, the organic enhancement layer may include an aromatic hydrocarbon material comprising an aromatic hydrocarbon core optionally substituted with any suitable substituent. The aromatic hydrocarbon core is an aromatic system containing no heterocyclic atoms in its rings. Suitable substituents are attached to the aromatic hydrocarbon core. Such suitable substituents may include elements other than hydrogen and carbon. Preferred substituents may be selected independently from the group consisting of alkyl, alkenyl, alkynyl, aryl, heteroalkyl, substituted aryl groups. Other substituents include substituted heteroaryl and heterocyclic groups. In addition, two or more of the same or different aromatic cores may be linked together to form a new core, which may be optionally substituted by alkyl, alkenyl, alkynyl, aryl, heteroalkyl, substituted aryl, substituted heteroaryl, and substituted heterocyclic groups.

In a preferred embodiment of the invention, the organic enhancement layer may include an aromatic non-heterocyclic hydrocarbon having the following structure:

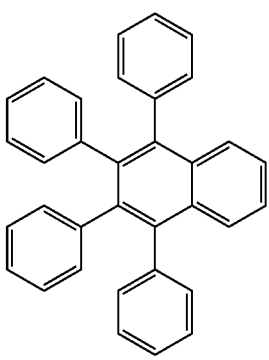

I

In another preferred embodiment of the invention, the organic enhancement layer may include an aromatic non-heterocyclic hydrocarbon having the following structure:

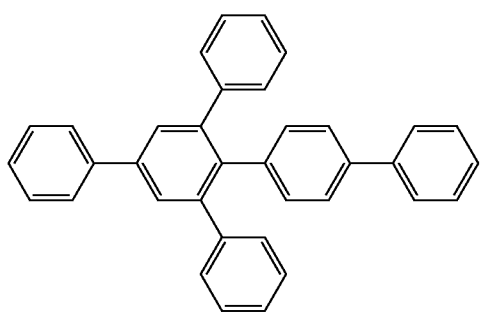

II

In another preferred embodiment of the invention, the organic enhancement layer may include an aromatic non-heterocyclic hydrocarbon having the following structure:

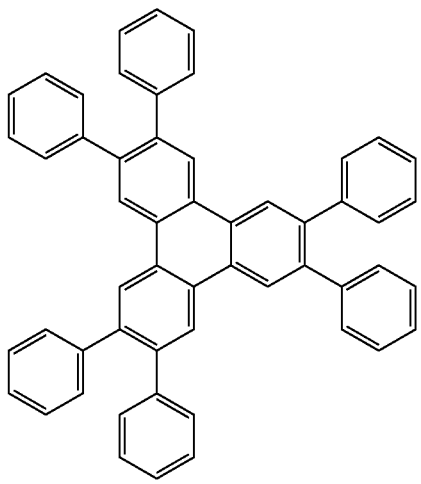

III

In another preferred embodiment of the invention, the organic enhancement layer may include an aromatic non-heterocyclic hydrocarbon having the following structure:

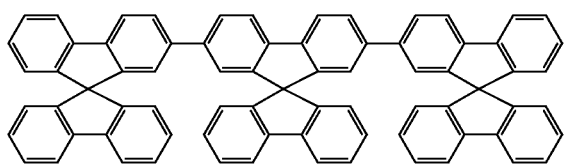

IV

In other embodiments of the invention, the organic enhancement layer may include an aromatic non-heterocyclic hydrocarbon having the following structures:

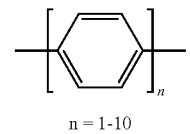

V n = 1-10

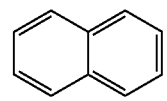

VI

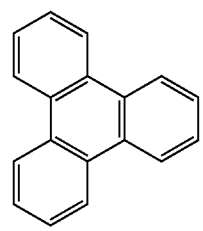

VII

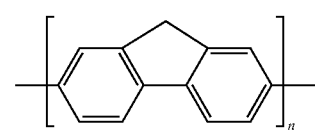

VIII n = 1-10

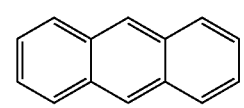

IX

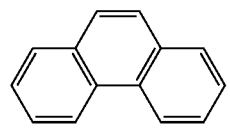

X

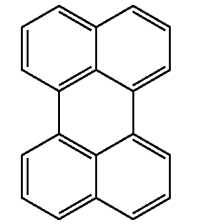

XI

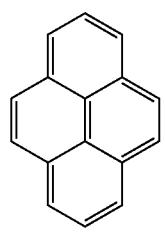

XII

In a preferred embodiment of the invention, the organic enhancement layer may include an aromatic non-heterocyclic hydrocarbon having the following structure:

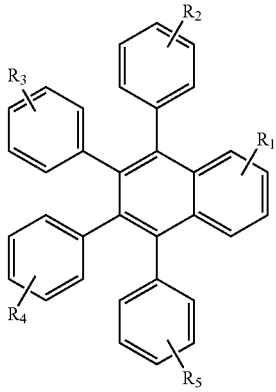

XIII such that $R_1$-$R_5$ each represent no substitution, mono-, di-, or tri-substitution, and wherein the substituents are the same or different, and each is selected from the group consisting of alkyl, alkenyl, alkynyl, aryl, heteroalkyl, and substituted aryl.

In another preferred embodiment of the invention, the organic enhancement layer may include an aromatic non-heterocyclic hydrocarbon having the following structure:

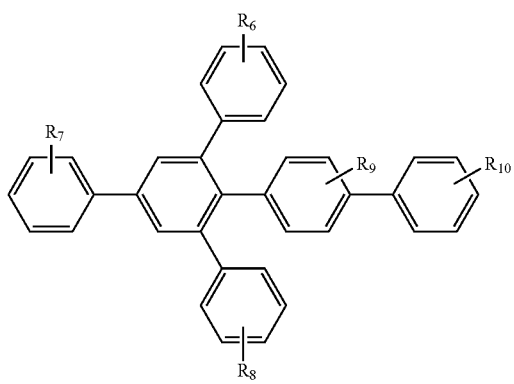

XIV such that $R_6$-$R_{10}$ each represent no substitution, mono-, di-, or tri-substitution, and wherein the substituents are the same or different, and each is selected from the group consisting of alkyl, alkenyl, alkynyl, aryl, heteroalkyl, and substituted aryl In another preferred embodiment of the invention, the organic enhancement layer may include an aromatic non-heterocyclic hydrocarbon having the following structure:

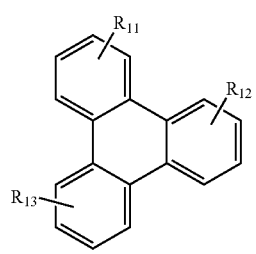

XV such that $R_{11}$-$R_{13}$ each represents no substitution, mono-, di-, or tri-substitution, and wherein $R_{11}$-$R_{13}$ are the same or different substituents, and each is selected from the group consisting of alkyl, alkenyl, alkynyl, aryl, heteroalkyl, and substituted aryl;

In another preferred embodiment of the invention, the organic enhancement layer may include an aromatic non-heterocyclic hydrocarbon having the following structure:

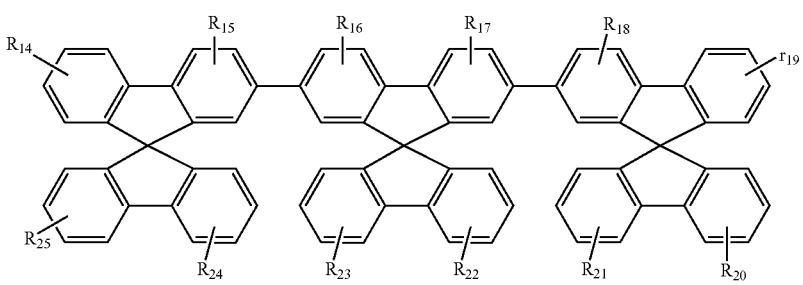

XVI such that $R_{14}$, $R_{19}$ and $R_{20}$-$R_{25}$ each represents no substitution, mono-, di-, tri-, or tetra-substitution, and $R_{15}$-$R_{18}$ each represent no substitution, mono-, di-, tri-substitution, and $R_{14}$-$R_{25}$ are the same or different substituents, and each is selected from the group consisting of alkyl, alkenyl, alkynyl, aryl, heteroalkyl and substituted aryl.

In other embodiments of the invention, the organic enhancement layer may include an aromatic non-heterocyclic hydrocarbon having the following structures:

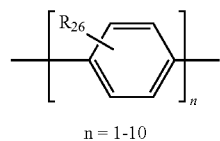

n = 1-10

XVII

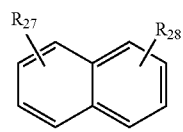

XVIII

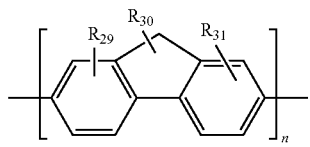

n = 1-10

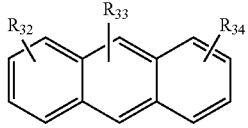

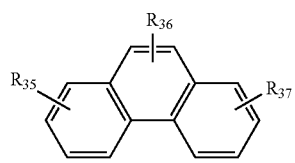

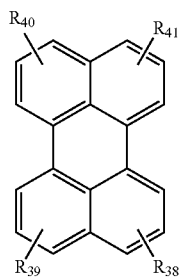

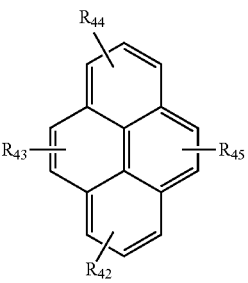

such that $R_{26}$-$R_{28}$ each represents no substitution, mono-, di-, or tri- or tetra-substitution, and $R_{29}$-$R_{45}$ each represent no substitution, mono-, di-, tri-substitution, and $R_{26}$-$R_{45}$ are the same or different substituents, and each is selected from the group consisting of alkyl, alkenyl, alkynyl, aryl, heteroalkyl and substituted aryl.

In other embodiments, the organic enhancement layer may include an aromatic hydrocarbon material having the following structures:

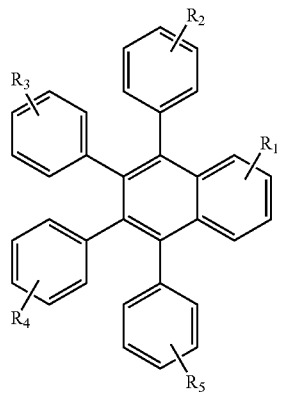

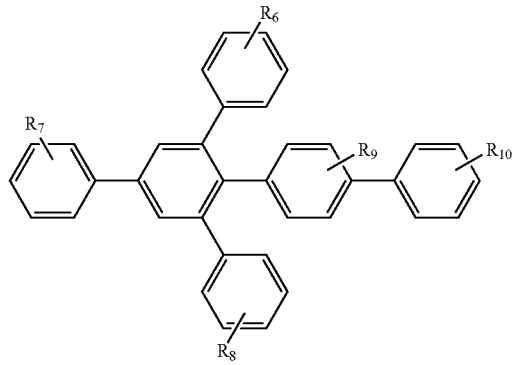

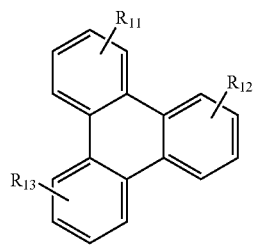

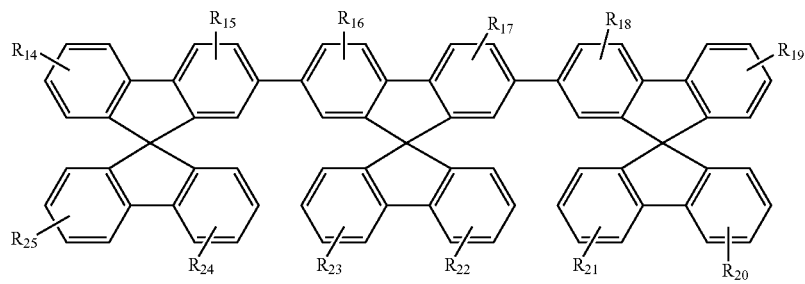

wherein $R_1$-$R_{10}$ each represent no substitution, mono-, di-, or tri-substitution, $R_{11}$-$R_{13}$, $R_{15}$-$R_{18}$ each represents no substitution, mono-, di-, or tri-substitution, and $R_{14}$, $R_{19}$, and $R_{20}$-$R_{25}$ each represents no substitution, mono-, di-, or tri- or tetra-substitution, and wherein $R_1$-$R_{25}$ are the same or different substituents, and each is selected from the group consisting of alkyl, alkenyl, aryl, heteroalkyl, substituted aryl, substituted heteroaryl and heterocyclic groups.

In another embodiment of the invention, the organic enhancement layer may include an aromatic hydrocarbon material having a core comprising at least 3 phenyl rings, wherein each phenyl ring in the core is fused or attached by a single C—C bond to at least one other phenyl ring in the core, and wherein the core is contiguous. In a contiguous core, each phenyl ring in the core is connected to every other phenyl ring in the core either directly, or by a chain of phenyl rings that are either fused or attached by a single C—C bond. Examples of ways that phenyl rings may be attached to other phenyl rings in a contiguous core are provided below:

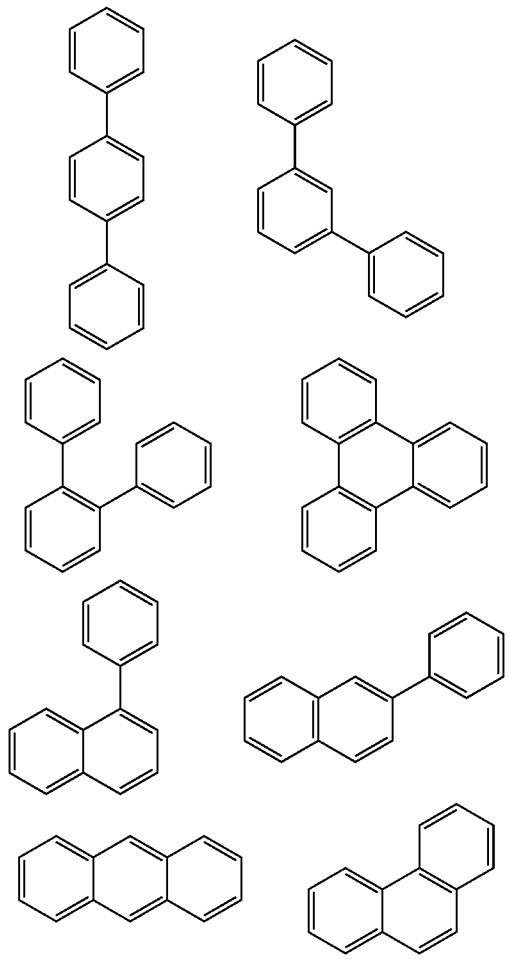

In another embodiment, the organic enhancement layer may include an aromatic hydrocarbon material having a core comprising at least 6 phenyl rings, wherein each phenyl ring in the core is fused or attached by a single C—C bond to at least one other phenyl ring in the core, and wherein the core is contiguous.

In another embodiment, a "core" may be defined as a group of least three phenyl rings, where each phenyl ring is π-conjugated to every other phenyl ring in the group. In this embodiment, a broader range of connections may be used between the phenyl rings, such as a chain of unsaturated carbon bonds.

In a typical phosphorescent device, it is believed that excitons are formed when electrons and holes meet and recombine in the emissive layer. It is also believed that this recombination generally occurs very close to where the electrons are injected into the emissive region. There are several possible reasons for this phenomenon. First, phosphorescent emissive materials may have superior hole transport properties, such that a phosphorescent emissive layer has a higher hole mobility than electron mobility, and holes are quickly transported across the emissive layer, as compared to electrons, which are more slowly transported. Second, holes may be injected into the emissive layer more readily than electrons. "Hole blocking" layers may be used to prevent holes from leaving the emissive layer. Some degree of hole blocking may occur where the hole blocking layer has a HOMO energy level lower than that of the adjacent layer, usually an emissive layer, from which holes are being blocked. Effective hole blocking layers generally have a HOMO energy level significantly lower than that of the adjacent layer, such as 0.25 eV lower, preferably, 0.3 eV lower, or, more preferably, 0.7 eV lower. The following table lists density function calculations (DFT) performed using the Spartan 02 software package with B31LYP/CEP-31G* basis set, with the pseudopotential option for materials containing heavy metals such as Ir(ppy)$_3$ or the Gaussian 98 software package with the B31LYP/CEP-31G* basis set where indicated by the symbol "#".

TABLE I

| | DFT | | |
|---|---|---|---|
| Compound | HOMO (eV) | LUMO (eV) | Dipole (D) |
| I | −5.66 | −1.01 | 0.24 |
| II | −5.66 | −1.05 | 0.13 |
| HPT | −5.54 | −1.29 | 0.01 |
| TSBF | −5.21 | −1.37 | 0.28 |
| CBP | −5.32 | −1.23 | 0.00 |
| fac-Ir(ppy)$_3$ | −4.85 | −1.21 | 6.14 |
| fac-Ir(ppy)$_3$# | −4.93 | −1.43 | 6.53 |
| fac-Ir(5-Phppy)$_3$# | −4.96 | −1.56 | 7.49 |
| TPBi | −5.70 | −1.25 | 5.63 |
| BCP | −5.87 | −1.17 | 2.89 |

Without necessarily being limited as to any particular theory as to how the invention works, it is believed that the organic enhancement layer may allow for efficient injection of electrons into the emissive layer. Instead of or in addition to "blocking" holes which then wait for electrons to trickle into the emissive layer, the organic enhancement layer may result in a flood of electrons that recombine with holes before they can reach the edge of the emissive layer. Superior electron injection properties may result from one of several properties of the organic enhancement layer material or materials.

In a preferred embodiment, the organic enhancement layer acts as both a hole blocking layer and provides superior electron injection. For example, compounds I and II have a HOMO that is 0.81 eV less than the HOMO of Ir(ppy)$_3$, a desirable phosphorescent emissive material. In a device where Ir(ppy)$_3$ is both the emissive material and provides the hole transport function in the emissive layer, for example, an organic enhancement layer of compound I or II may block holes due to the large HOMO level difference of 0.81 eV, and may also provide superior electron injection. Depending upon the hole transport properties of the emissive layer, other HOMO energy level differences may be utilized in accordance with embodiments of the invention to achieve both hole blocking and superior electron injection.

In one embodiment, the use of an organic enhancement layer including an aromatic hydrocarbon material having a low molecular dipole moment may result in superior device performance. Without intending to limit all embodiments with a particular theory of how the invention works, it is believed that a low molecular dipole moment may improve electron injection from the organic layer into the emissive layer, because the presence of a significant molecular dipole moment may lead to a local electric field that can trap or slow down charge migration. As a result, the material may inject electrons into the emissive layer rapidly enough that a significant proportion of holes in the organic emissive layer encounter an electron and recombine before reaching the interface between the organic enhancement layer and the emissive layer. In some embodiments of the invention, the second organic layer does not have energetics suitable for hole blocking, because hole blocking may not be needed due to superior electron injection. The organic enhancement layer may have a HOMO energy level that is not generally considered effective as a hole blocking layer. For example, the HOMO energy level of the second organic layer may be greater than that of the emissive layer, in which case no hole blocking at all would be expected. By way of further example, the HOMO energy level of the organic enhancement layer may be less than that of the emissive layer, but the difference may be so small that significant hole blocking is not expected. For example, the difference in energy levels may be less than about 0.25 eV, about 0.3 eV, or about 0.7 eV.

In one embodiment, it is believed that the use of an organic enhancement layer including an aromatic hydrocarbon having a zero or low molecular dipole moment may result in superior device performance. Without intending to limit all embodiments with a particular theory of how the invention works, it is believed that this symmetric energy structure may improve electron injection from the organic enhancement layer into the emissive layer because the symmetry in the HOMO and LUMO of the aromatic hydrocarbon molecules may lead to reduce dipole induced charge trap sites, thus better charge hopping between the molecules as compared to heterocyclic analogs which may have localized electron density associated with heterocyclic systems. In addition, it is also believed that the lack of heteroatoms and delocalized electron density in the core structures of the aromatic hydrocarbons of the present invention lead to a better delocalization and stabilization when the aromatic hydrocarbon is oxidized (cation radical) or reduced (anion radical). This results in a lower susceptibility to bond breaking in the aromatic hydrocarbons, and thus higher stability in devices incorporating these materials compared to heterocyclic aromatics. Further, the lack of polar substituents such as halogen (I, Br, Cl, and F), and CN on the aromatic hydrocarbon may serve the same purpose since polar groups tend to perturb the electron density distribution on the aromatic ring, making the bonds on the ring more susceptible to rupture. Superior electron injection may enable superior device performance without necessarily using a blocking layer, as described above with respect to low molecular dipole moment materials.

"Stability" may be measured in a number of ways. One stability measurement is the operational stability of the electroluminescent device. The operational half-life is the time required for the luminance of the device to decay from the initial luminance ($L_0$) to 50% of its initial luminance ($L_{0.5}$) under constant direct current drive and at room temperature unless otherwise noted. Operational half-life depends upon luminance at which the device is operated, because a higher luminance generally corresponds to a faster decay in a particular device. Devices in accordance with embodiments of the present invention can advantageously have an operational half-life in excess of about 1000 hours at an initial luminance of about 100 to about 1000 $cd/m^2$.

In another embodiment, the organic enhancement layer may comprise a material having a low molecular dipole moment, wherein a low molecular dipole moment means a molecular dipole moment of less than about 2.0 debyes, such that the device has an unmodified external quantum efficiency of at least about 3%; a highest occupied molecular orbital that is not more than 0.8 eV less than the highest occupied molecular orbital of the hole transporting material in the adjacent organic layer; and a lifetime of at least about 1000 hours at an initial luminance of about 100 to about 1000 $cd/m^2$. In another embodiment, the organic enhancement layer may comprise a material having a highest occupied molecular orbital that is at least about 0.8 eV greater than the highest occupied molecular orbital of the hole transporting material in the adjacent first organic layer, such that the device has an unmodified external quantum efficiency of at least about 5% and a lifetime of at least about 1000 hours at an initial luminance of about 100 to about 1000 $cd/m^2$. In yet another embodiment, the organic enhancement layer may comprise a material having a molecular dipole moment less than about 2.0 debyes, such that the device has an external quantum efficiency of at least about 5% at from about 100 to about 1000 $cd/m^2$. The organic enhancement layer may be in direct contact with the cathode, or there may be a separate organic layer between the organic enhancement layer and the cathode. Other aromatic hydrocarbon materials may be used.

As used herein, the term "external quantum efficiency" refers to the percentage of charge carriers injected into a device that result in the emission of a photon from the device in the forward direction. A number of factors can affect the external quantum efficiency, including the "internal quantum efficiency," which is the percentage of charge carriers injected into a device that result in the creation of a photon, and the "outcoupling efficiency," which is the percentage of photons created that are emitted from a device towards a viewer. Many embodiments of the present invention are directed to an organic layer comprising an aromatic hydrocarbon layer that is in direct contact with an emissive layer, which may enhance the internal quantum efficiency and thus the external quantum efficiency of the device. Because external quantum efficiency is more readily and directly measured than internal quantum efficiency, it may be desirable to describe certain aspects of the invention with respect to external quantum efficiency. However, in order to determine whether an enhanced external quantum efficiency is due to the use of an aromatic hydrocarbon, it is preferable to account for other factors that affect external quantum efficiency. The term "unmodified external quantum efficiency" as used herein refers to the external quantum efficiency of a device, after multiplication by a factor to account for any differences in the outcoupling efficiency of that device and the outcoupling efficiency of the devices described experimentally herein. For example, a device having an external quantum efficiency of 5%, but having an outcoupling efficiency 3 times better than the devices described herein, would have an "unmodified external quantum efficiency" of 1.33% (one third of 5%). A typical outcoupling efficiency for the types of devices described herein is about 20-30%. There are device structures having better outcoupling efficiencies than the devices described herein, and it is anticipated that improvements to outcoupling efficiency will be made over time. Such improvements would enhance external quantum efficiency, but should not affect "unmodified" external quantum efficiency, and devices having such improvements may fall within the scope of the present invention.

As electrons are expected to reside primarily on the LUMO, molecules with higher symmetry may show greater delocalization of the negative charge over the molecule. The enhanced delocalization of charge may increase the bulk conductivity, electron mobility, and operational stability properties in a device.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting. While many embodiments of the invention allow for superior device performance in the absence of hole blocking, it is understood that some embodiments of the invention may be combined with hole blocking.

MATERIAL DEFINITIONS

As used herein, abbreviations refer to materials as follows:

| | |
|---|---|
| CBP: | 4,4'-N,N-dicarbazole-biphenyl |
| m-MTDATA | 4,4',4''-tris(3-methylphenylphenylamino)triphenylamine |
| Alq$_3$: | aluminum(III) tris(8-hydroxyquinolate) |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F$_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine |
| ITO: | indium tin oxide |
| NPD: | N,N'-diphenyl-N-N'-di(1-naphthyl)-benzidine |
| TPD: | N,N'-diphenyl-N,N'-di(3-toly)-benzidine |
| BAlq: | aluminum(III)bis(2-methyl-8-hydroxyquinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT:PSS : | an aqueous dispersion of poly(3,4-ethylenedioxythiophene) with polystyrenesulfonate (PSS) |
| ZrQ$_4$: | zirconium(IV) tetrakis(8-hydroxyquinolate) |
| HfQ$_4$: | hafnium(IV) tetrakis(8-hydroxyquinolate) |
| GaQ$_3$: | gallium(III) tris(8-hydroxyquinolate) |
| PBD: | 2-(4-biphenylyl)-5-phenyl-1,3,4-oxidiazole |
| TPBi: | 2,2',2''-(1,3,5-benzenetriyl)tris-(1-phenyl-1H-benzimidazole) |
| Boron 1: | 1,4-Bis(diphenylboronyl)benzene |
| Boron 2: | Tris(2,3,5,6-tetramethylphenyl)borane |
| HPT: | 2,3,6,7,10,11-hexaphenyltriphenylene |
| TSBF: | ter-2, 7-spirobifluorene |
| Ir(5-Phppy)$_3$: | tris [5-phenyl(2-phenylpyridine)]iridium(III) |
| Ir(3'-Mepq)$_2$(acac) | bis[3'-methyl(2-phenylquinoline)]iridium(III) acetylacetonate |

EXPERIMENTAL

Specific representative embodiments of the invention will now be described, including how such embodiments may be made. It is understood that the specific methods, materials, conditions, process parameters, apparatus, and the like do not necessarily limit the scope of the invention.

Example 1

Synthesis of 3',5'-diphenyl-p-quaterphenyl (Compound II)

Step 1

Preparation of Sodium 4-Biphenylacetate

4-Biphenylacetic acid (25.0 g, 0.1177 mol.) and sodium hydroxide (4.71 g, 0.1177 mol.) were dissolved in 50 mL of water and stirred at room temperature for 2 hours. The product was isolated by evaporating off the water.

Step 2

Preparation of 3',5'-diphenyl-p-quaterphenyl

Sodium 4-biphenylacetate (25.0 g, 0.106 mol.) was placed in a suspension of 2,4,6-triphenylpyrylium tetrafluoroborate (41.0 g, 0.106 mol.) in 80 mL of acetic anhydride under nitrogen atmosphere and refluxed for 24 hours. The crude product was extracted with a 7:3 ratio mixture of hexane/dichloromethane. The solvent was stripped, and the crude product sublimed 4 times to achieve 99% purity. The practical yield following sublimations was 20%.

Example 2-3 and Comparative Examples 4-5

Experimental Device Fabrication

All devices were fabricated using thermal evaporation at a pressure of $<1\times10^{-7}$ Torr. The devices were fabricated on a glass substrate precoated with a 120 nm thick anode of indium tin oxide (ITO), commercially available from Applied Films of Longmont, Colo. The cathode was 1 nm of LiF followed by 100 nm of aluminum. All devices were encapsulated with a glass lid sealed with an epoxy resin under nitrogen (<1 ppm H$_2$O and O$_2$) immediately after fabrication, and a moisture getter was incorporated inside each device. Device lifetime is defined as the time required for the luminance to decrease from its initial value to 50% of the initial value, at room temperature under constant DC drive.

Current-voltage-luminance characteristics and operational lifetime were measured and are summarized in Table II, below. A typical display brightness level of 600 cd/m$^2$ for green emitting devices was chosen for purposes of comparison between devices.

The organic stack was fabricated to consist of CuPc as a hole injection layer at a thickness of 10 nm; NPD as a hole transport layer at a thickness of 30 nm; CBP doped with 6 wt % Ir(ppy)$_3$ as the emissive layer at a thickness of 30 nm. Adjacent to the emissive layer was an electron transport layer, ETL2, consisting of 10 nm of an aromatic hydrocarbon (Compounds I and II described above) or, for the comparative examples, a heterocyclic aromatic hydrocarbon. Adjacent to layer ETL2 was an electron transport layer consisting of Alq$_3$ at a thickness of 40 nm.

TABLE II

| Example | ETL2 material | Efficiency (cd/A, %) at 600 cd/m² | % luminance retained at 100 hours at initial luminance of 600 cd/m² |
|---|---|---|---|
| 2 | Compound I | 21, 6.0 | 95 |
| 3 | Compound II | 29, 8.2 | 90 |
| 4 | TPBi | 22, 6.1 | 75 |
| 5 | BCP | 35, 9.7 | 85 |

Additional testing of the device of example 3 yielded a retention of 70% of the initial luminance at 650 hours (initial luminance was 600 cd/m²).

Example 6

Synthesis of 2,3,6,7,10,11-hexaphenyltriphenylene (HPT)

Step 1

Preparation of 2,3,6,7,10,11-hexabromotriphenylene 2,3,6,7,10,11-Hexabromotriphenylene was prepared according to the literature method (Breslow et al, Tetrahedron, 1982, 38, 863). Triphenylene (3.0 g, 13.2 mmol) was dissolved in 70 mL of nitrobenzene. 0.27 g of Fe powder was added. To this mixture, bromine (18.6 g, 120 mmol) in 20 mL of nitrobenzene was added via a dropping funnel. The mixture was stirred at room temperature for 12 hours and brought to reflux for 2 hours. After cooling, the solid was filtered, washed with ethanol, and dried. 8.9 g (96%) of crude product was obtained. Recrystallization in boiling 1,2-dichlorobenzene (~180° C.) yielded the product as off-white needles (8.64 g, 94%). The product was confirmed by mass spectrometry.

Step 2

Preparation of 2,3,6,7,10,11-hexaphenyltriphenylene (HPT)

2,3,6,7,10,11-hexabromotriphenylene (8.64 g, 12.3 mmol), phenylboronic acid (13.5 g, 111 mmol), triphenylphosphine (0.64 g, 2.46 mmol), Pd(OAc)$_2$ (0.14 g, 0.615 mmol), K$_2$CO$_3$ (20.4 g, 147.6 mmol) were in 600 mL of xylenes and 50 mL of water. The mixture was purged with nitrogen for 5 minutes and slowly brought to reflux under nitrogen. TLC (CH$_2$Cl$_2$:hexane ~1:2 v/v, the starting hexabromo compound did not move) showed the appearance of a new spot (xylenes also showed up on the TLC but it eluted up faster than the product) within hours. The mixture was refluxed for 12 hours. After cooling, the solid was filtered, washed with ethanol, and dried. The crude yield was higher than 90%. Recrystallization in xylenes (~100 mL per 3-4 g of product) yield white crystals. Vacuum sublimation yielded the product (~4.5 g) which was confirmed by NMR and mass spectrometry.

Example 7

Synthesis of ter-2,7-spirobifluoroene (TSBF)

TSBF was synthesized according to Wong, et. al. *J. Am. Chem. Soc.*, 2002, 124, 11576-11577. The product was purified by vacuum sublimation.

Device Fabrication and Measurement

All devices were fabricated by high vacuum (<10⁻⁷ Torr) thermal evaporation. The anode electrode was ~1200 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The current-voltage-luminance (IVL) characteristics were measured. The luminous efficiency and operational lifetime are summarized in the Table III. A typical display brightness level of 600 cd/m² is chosen for the comparison between different devices. Device operational stability was measured at room temperature under constant direct current of 40 mA/cm² or at initial luminance (L$_0$) of 955 nits; or at 60° C. under constant direct current at L$_0$=955 cd/m². The halflife (T$_{1/2}$) is defined as the time required for the L$_0$ to drop to 50% of L$_0$.

Example 8

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 4.5 wt % of Ir(5-Phppy)$_3$ as the emissive layer (EML). The ETL2 was 100 Å of HPT. The ETL1 was 400 Å of tris(8-hydroxyquinolinato) aluminum (Alq$_3$).

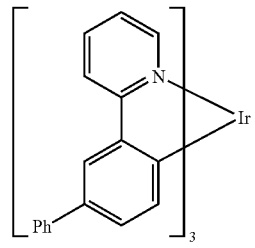

Ir(5-Phppy)$_3$

Example 9

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 6 wt % of Ir(5-Phppy)$_3$ as the emissive layer (EML). The ETL2 was 100 Å of HPT. The ETL1 was 400 Å of tris(8-hydroxyquinolinato) aluminum (Alq$_3$).

Example 10

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 12 wt % of Ir(5-Phppy)$_3$ as the emissive layer (EML). The ETL2 was 100 Å of HPT. The ETL1 was 400 Å of tris(8-hydroxyquinolinato) aluminum (Alq$_3$).

Comparative Example 11

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 4.5 wt % of Ir(5-Phppy)$_3$ as the emissive layer (EML). The ETL2 was 100 Å of aluminum(III) bis(2-methyl-8-hydroxyquinolinato)-4-phenylphenolate (BAlq). The ETL1 was 400 Å of tris(8-hydroxyquinolinato)aluminum (Alq$_3$).

Example 12

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 12 wt % of Ir(5-Phppy)$_3$ as the emissive layer (EML). The ETL2 was 400 Å of HPT. There was no ETL1.

Example 13

The organic stack consisted of 100 Å thick of copper phthalocyanine (CuPc) as the hole injection layer (HIL), 400 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 12 wt % of Ir(3'-Mepq)$_2$(acac) as the emissive layer (EML). The ETL2 was 100 Å of HPT. The ETL1 was 400 Å of tris(8-hydroxyquinolinato)aluminum (Alq$_3$).

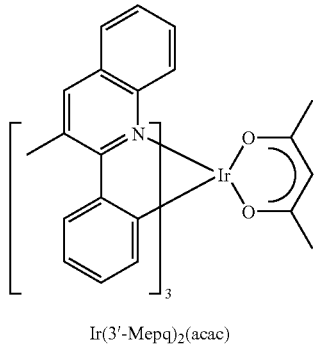

Ir(3'-Mepq)$_2$(acac)

Comparative Example 14

The organic stack consisted of 100 Å thick of copper phthalocyanine (CuPc) as the hole injection layer (HIL), 400 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 12 wt % of Ir(3'-Mepq)$_2$(acac) as the emissive layer (EML). The ETL2 was 150 Å of aluminum(III) bis(2-methyl-8-hydroxyquinolinato) 4-phenylphenolate (BAlq). The ETL1 was 400 Å of tris(8-hydroxyquinolinato)aluminum (Alq$_3$).

Example 15

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 4.5 wt % of Ir(5-Phppy)$_3$ as the emissive layer (EML). The ETL2 was 400 Å of TSBF. There was no ETL1.

Example 16

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 4.5 wt % of Ir(5-Phppy)$_3$ as the emissive layer (EML). The ETL2 was 100 Å of TSBF. The ETL1 was 300 Å of aluminum(III)bis(2-methyl-8-hydroxyquinolinato) 4-phenylphenolate (BAlq).

Example 17

The organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 4.5 wt % of Ir(5-Phppy)$_3$ as the emissive layer (EML). The ETL2 was 100 Å of TSBF. The ETL1 was 300 Å of tris(8-hydroxyquinolinato) aluminum (Alq$_3$).

TABLE III

| Example | ETL2 Material | ETL1 Material | Luminous Efficiency (cd/A) at 600 cd/m$^2$ | $T_{1/2}$ (hour) at J = 40 mA/cm$^2$ |
| --- | --- | --- | --- | --- |
| 8 | HPT | Alq | 37.4 | 350 |
| 9 | HPT | Alq | 40.3 | 377 |
| 10 | HPT | Alq | 43.4 | 234 |
| Comparative 11 | BAlq | Alq | 28.1 | 350 |
| 12 | HPT | none | 18.3 | not tested |
| 13 | HPT | Alq | 14.3 | 100 |
| Comparative 14 | BAlq | Alq | 13.6 | 250 |
| 15 | TSBF | none | 18.2 | 14 |
| 16 | TSBF | BAlq | 16.7 | 300 |
| 17 | TSBF | Alq | 26.7 | 140 |

Figure 5:
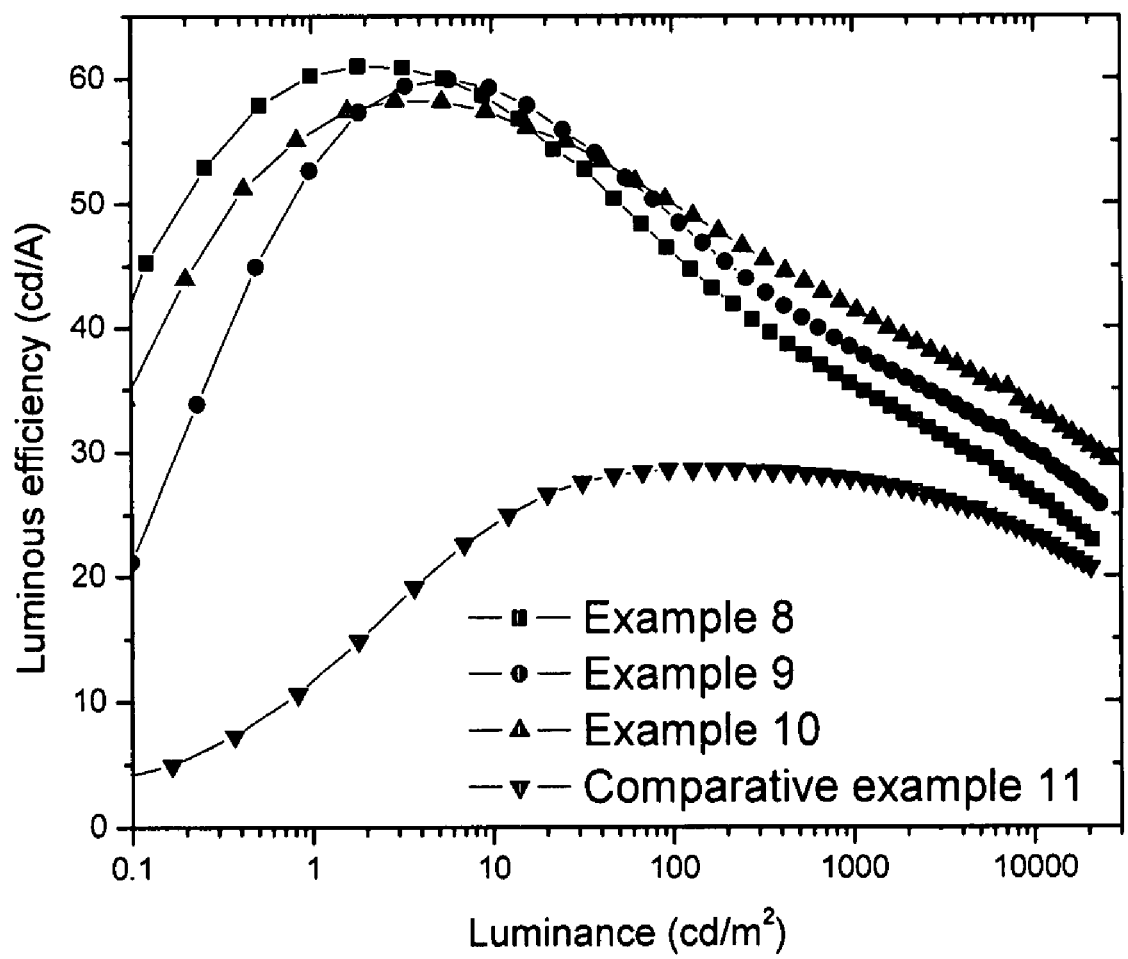
FIG. 5 shows luminous efficiency vs. brightness for examples 8-10 and comparative example 11.
Figure 6:
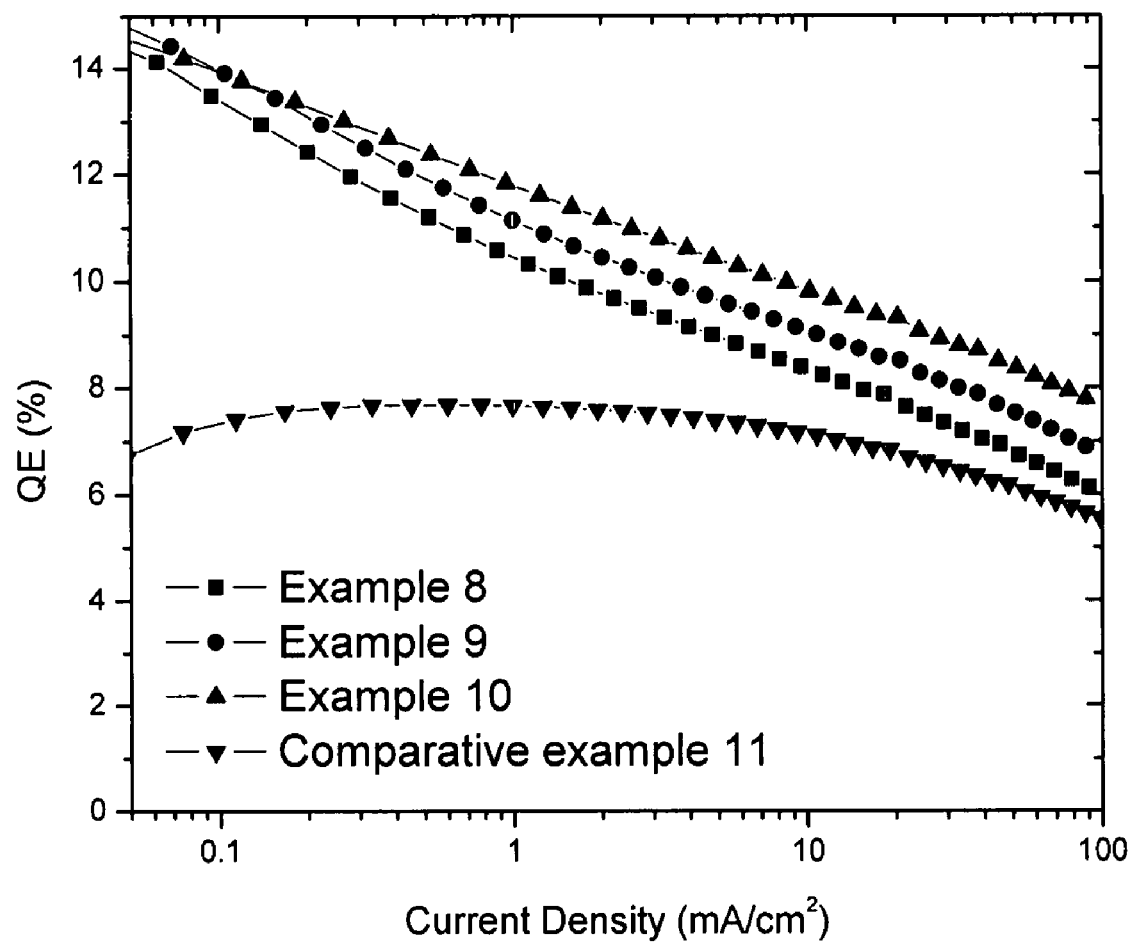
FIG. 6 shows external quantum efficiency vs. current density for examples 8-10 and comparative example 11.

FIG. 5 shows luminous efficiency vs. brightness for examples 8-10 and comparative example 11. FIG. 6 shows external quantum efficiency vs. current density for examples 8-10 and comparative example 11. Higher efficiencies are demonstrated by examples 8-10 which utilize HPT as the ETL2 compared to example 11 which utilizes BAlq as the ETL2.

Figure 7:
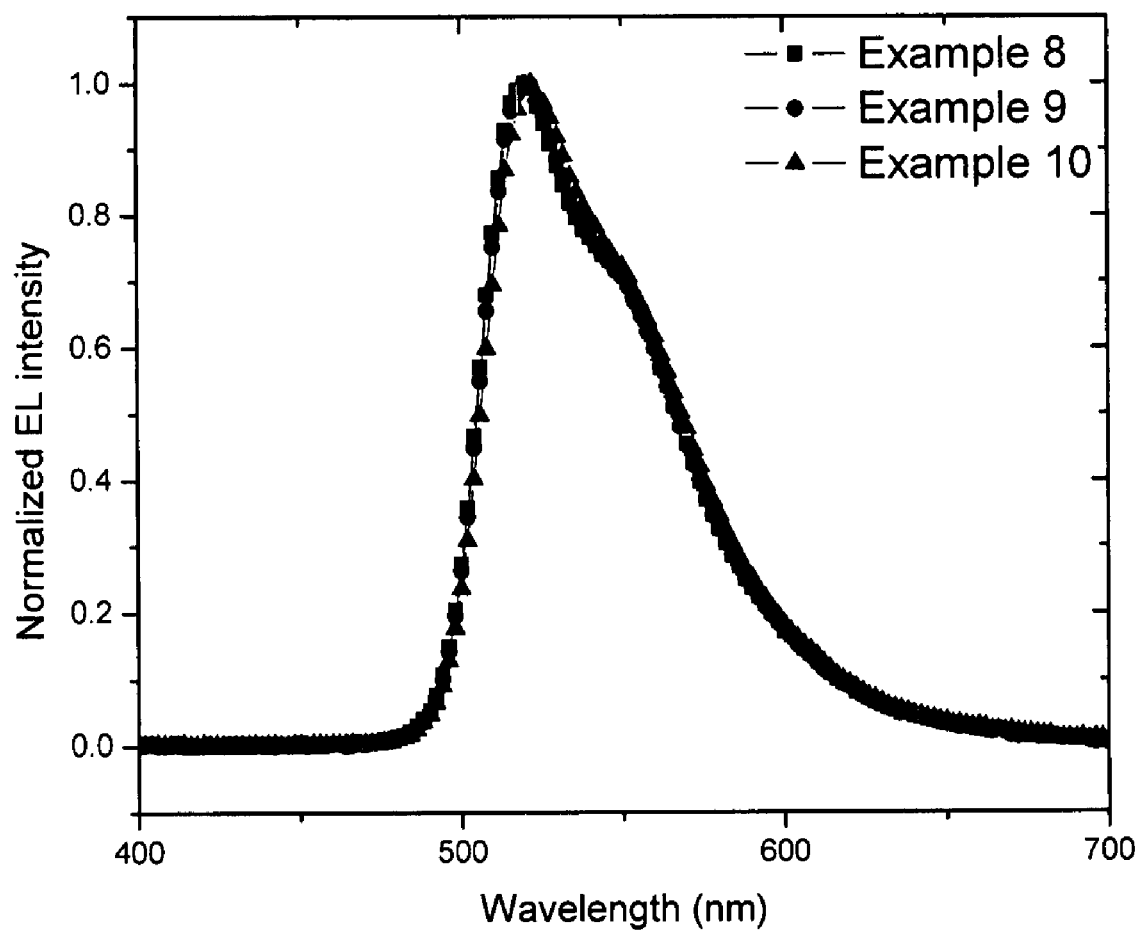
FIG. 7 shows normalized electroluminescence spectra for examples 8-10 using HPT as the ETL2.

FIG. 7 shows the normalized electroluminescence spectra for examples 8-10 which utilize HPT as the ETL2. There is no change in the spectra upon varying the dopant concentration of Ir(5-Phppy)$_3$ in the EML from 4.5% to 12%.

Figure 8:
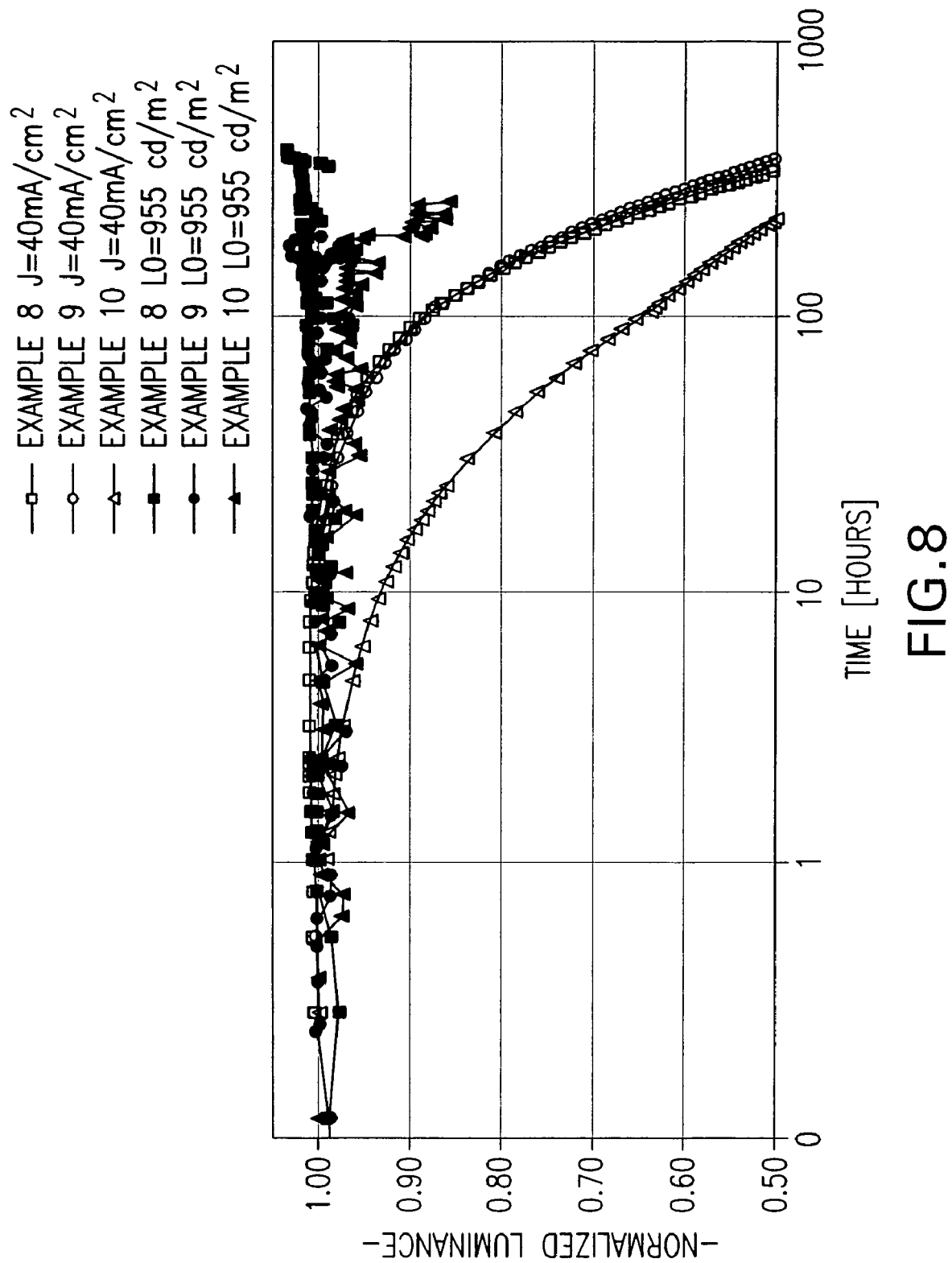
FIG. 8 operational stability for examples 8-10 using HPT as the ETL2 at room temperature under constant direct current of 40 mA/cm² and at initial luminance ($L_0$) of 955 nits.

FIG. 8 shows the operational stability for examples 8-10 which utilize HPT as the ETL2 at room temperature under constant direct current of 40 mA/cm$^2$ and at initial luminance (L$_0$) of 955 nits.

Figure 9:
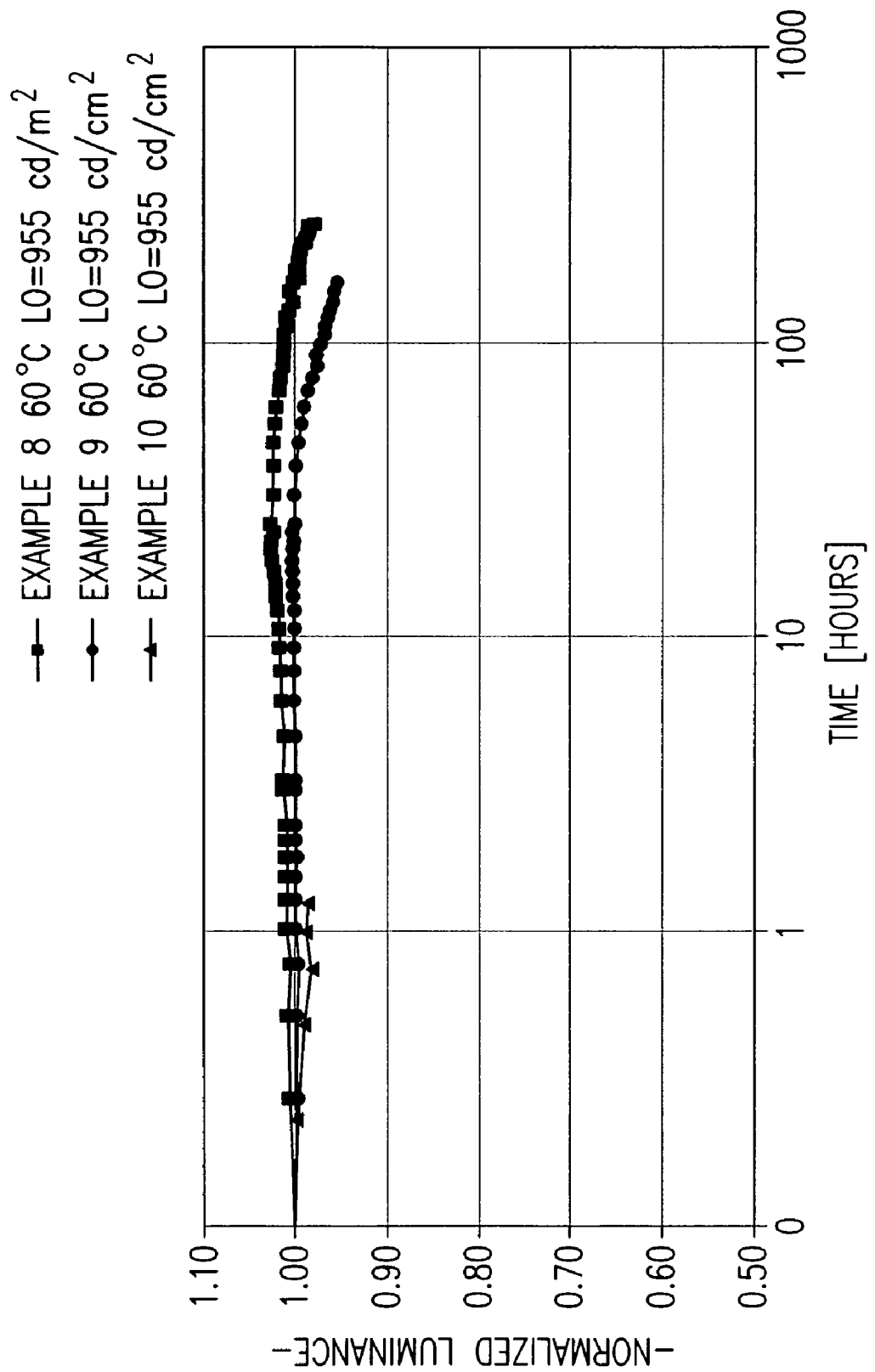
FIG. 9 shows the operational stability for examples 8-10 using HPT as the ETL2 at 60° C. under constant direct current at $L_0$=955 cd/m².

FIG. 9 shows the operational stability for examples 8-10 which utilize HPT as the ETL2 at 60° C. under constant direct current at L$_0$=955 cd/m$^2$.

Figure 10:
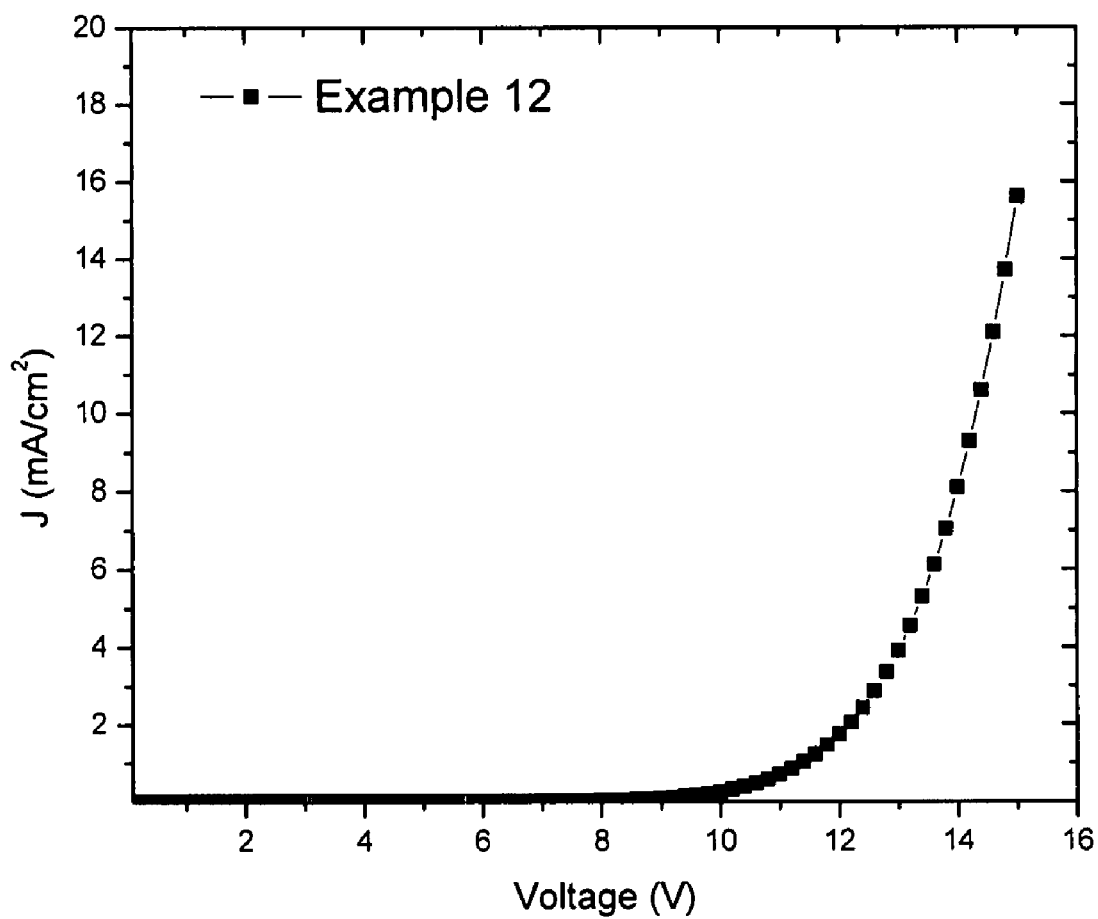
FIG. 10 shows the current-voltage characteristics for example 12.

FIG. 10 shows the current-voltage characteristics for example 12. Higher voltage is required to operate compared to examples 8-10.

Figure 11:
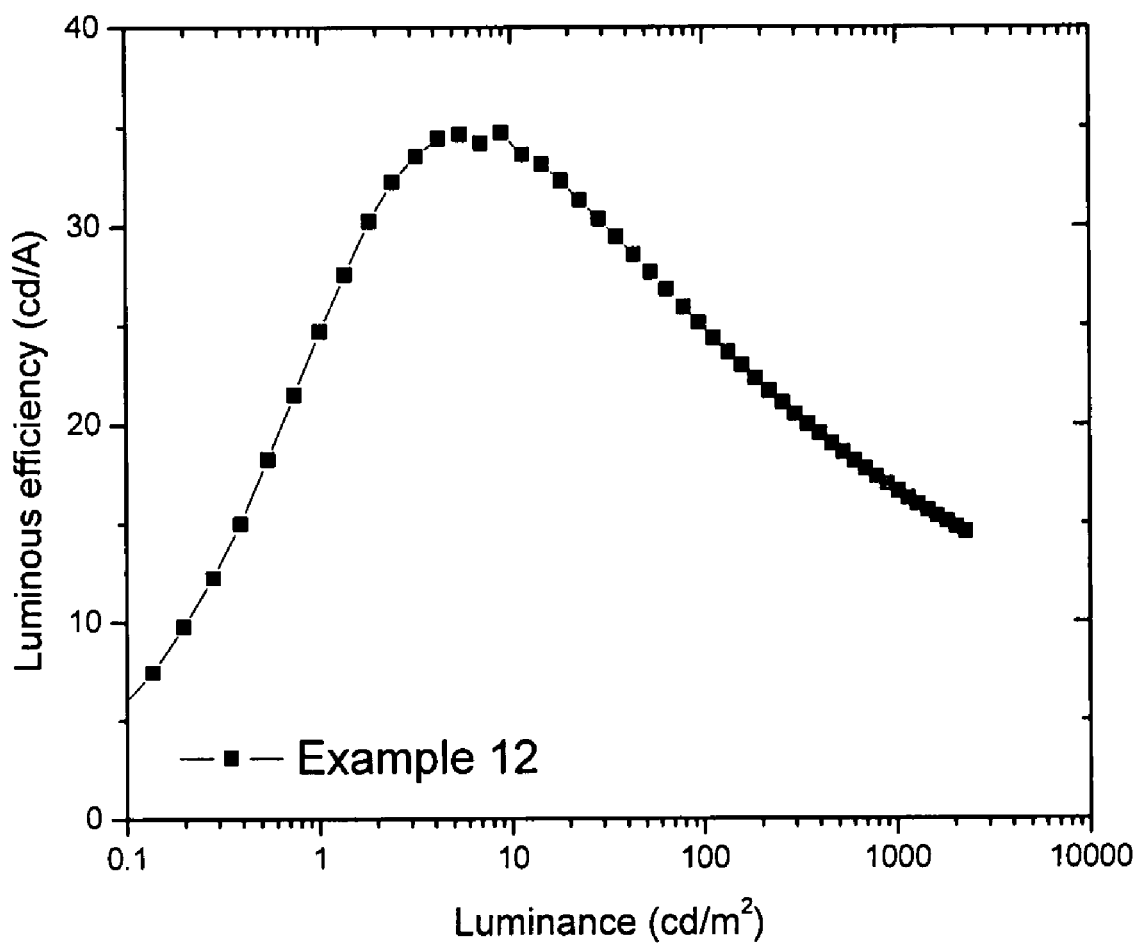
FIG. 11 shows luminous efficiency vs. brightness for example 12.
Figure 12:
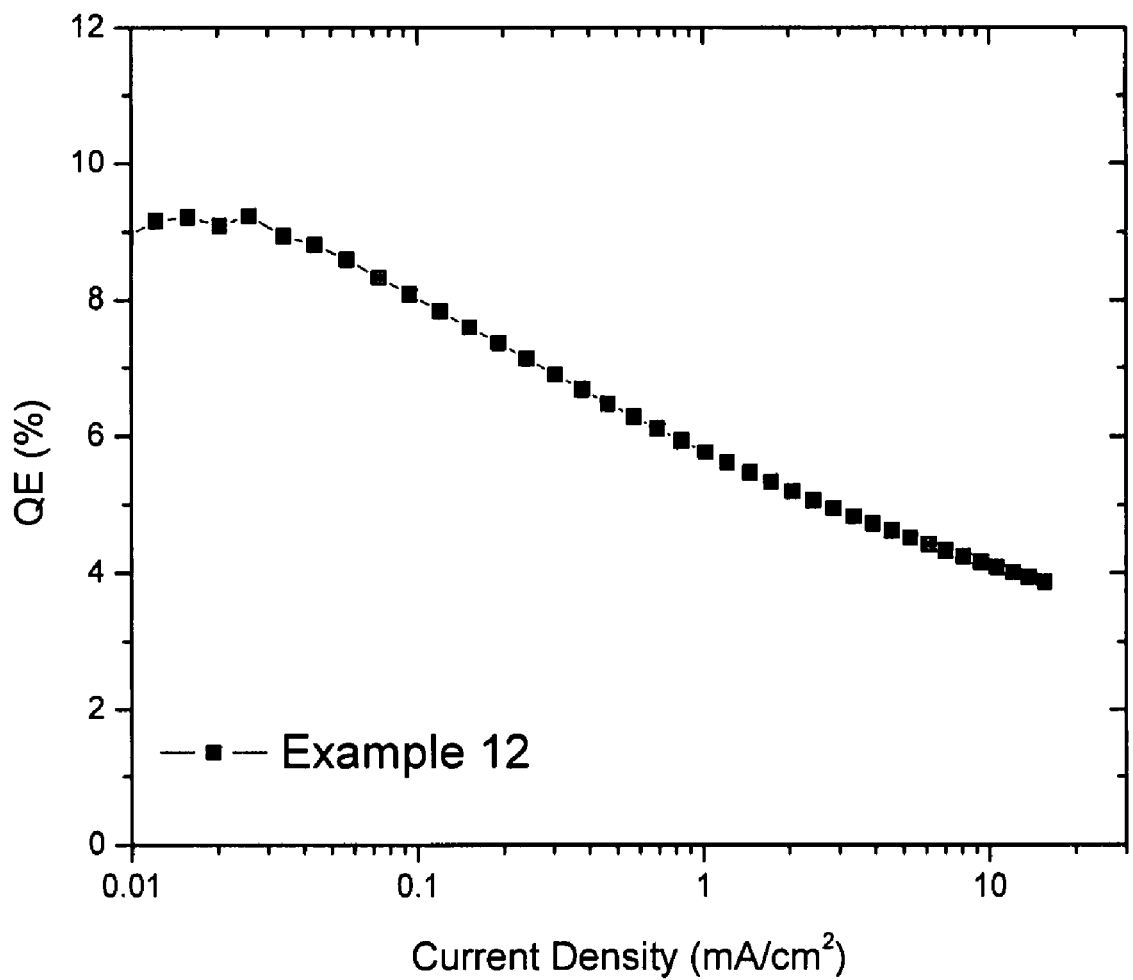
FIG. 12 and external quantum efficiency vs. current density for example 12.

FIG. 11 shows the luminous efficiency vs. brightness for example 12. FIG. 12 shows the external quantum efficiency vs. current density for example 12. Lower efficiencies are obtained compared to examples 8-10.

Figure 13:
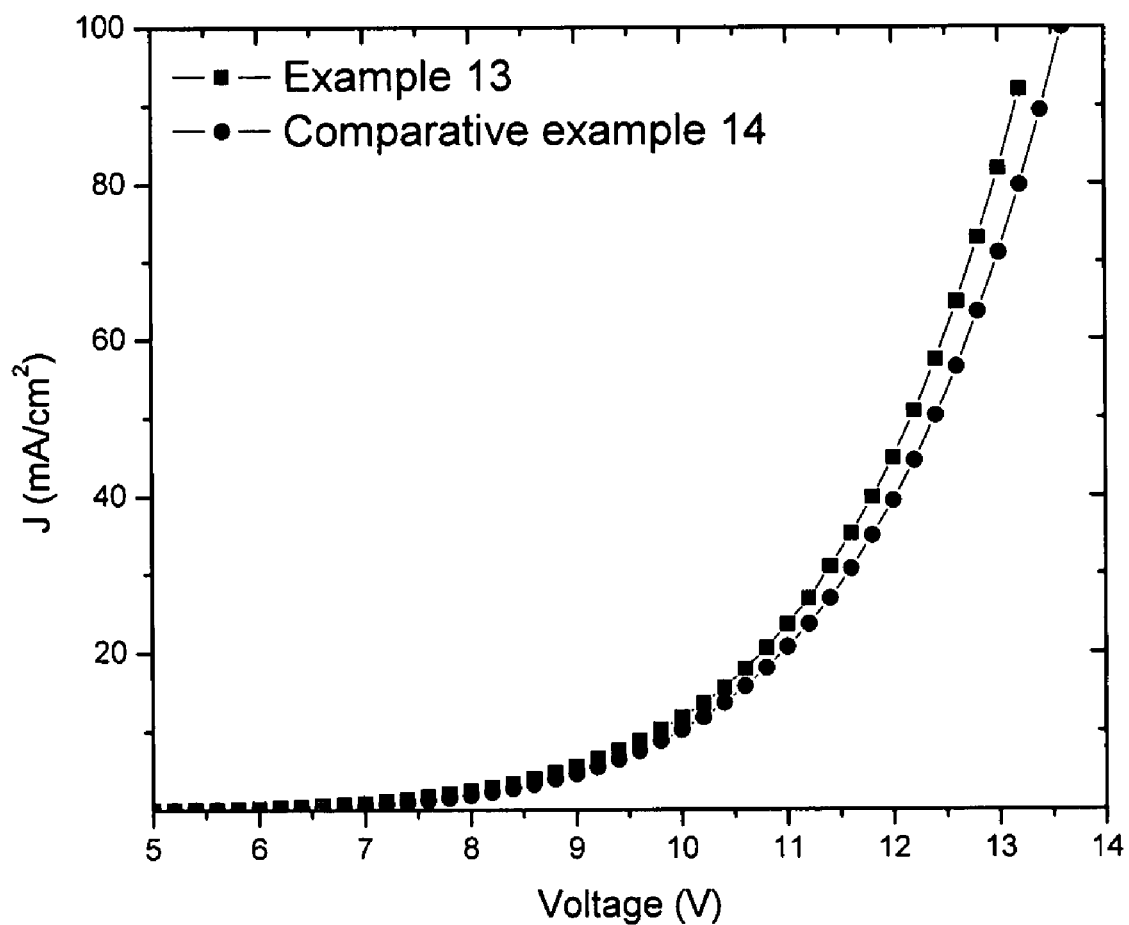
FIG. 13 shows the current-voltage characteristics for examples 13 and comparative example 14.

FIG. 13 shows the current-voltage characteristics for examples 13 and comparative example 14. Lower voltage is required to operate example 13 which utilize HPT as the ETL2 compared to example 14 which utilizes BAlq as the ETL2.

Figure 14:
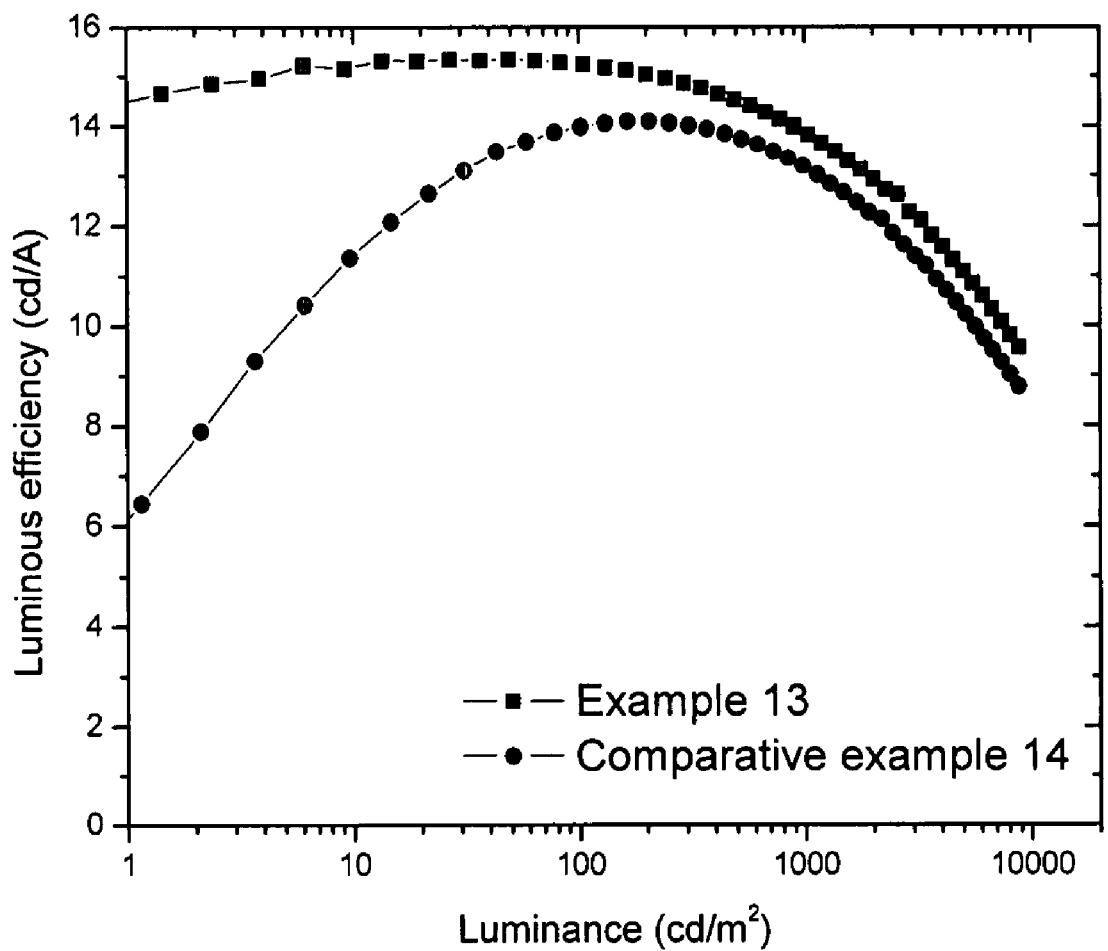
FIG. 14 luminous efficiency vs. brightness for example 13 and comparative example 14.
Figure 15:
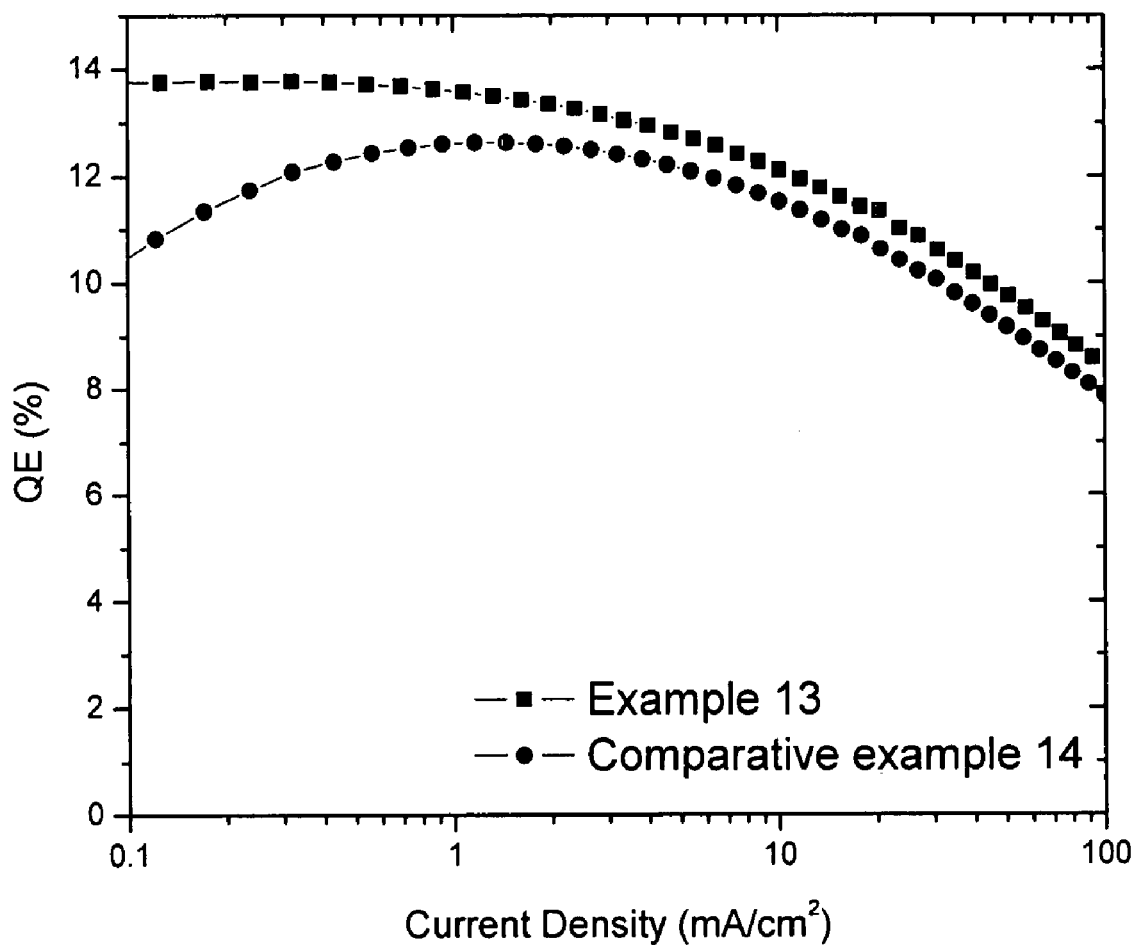
FIG. 15 external quantum efficiency vs. current density for example 13 and comparative example 14 using HPT as the ETL2.

FIG. 14 shows luminous efficiency vs. brightness for example 13 and comparative example 14. FIG. 15 shows external quantum efficiency vs. current density for example 13 and comparative example 14. Higher efficiencies are demonstrated by example 13 which utilize HPT as the ETL2 compared to example 14 which utilizes BAlq as the ETL2.

Figure 16:
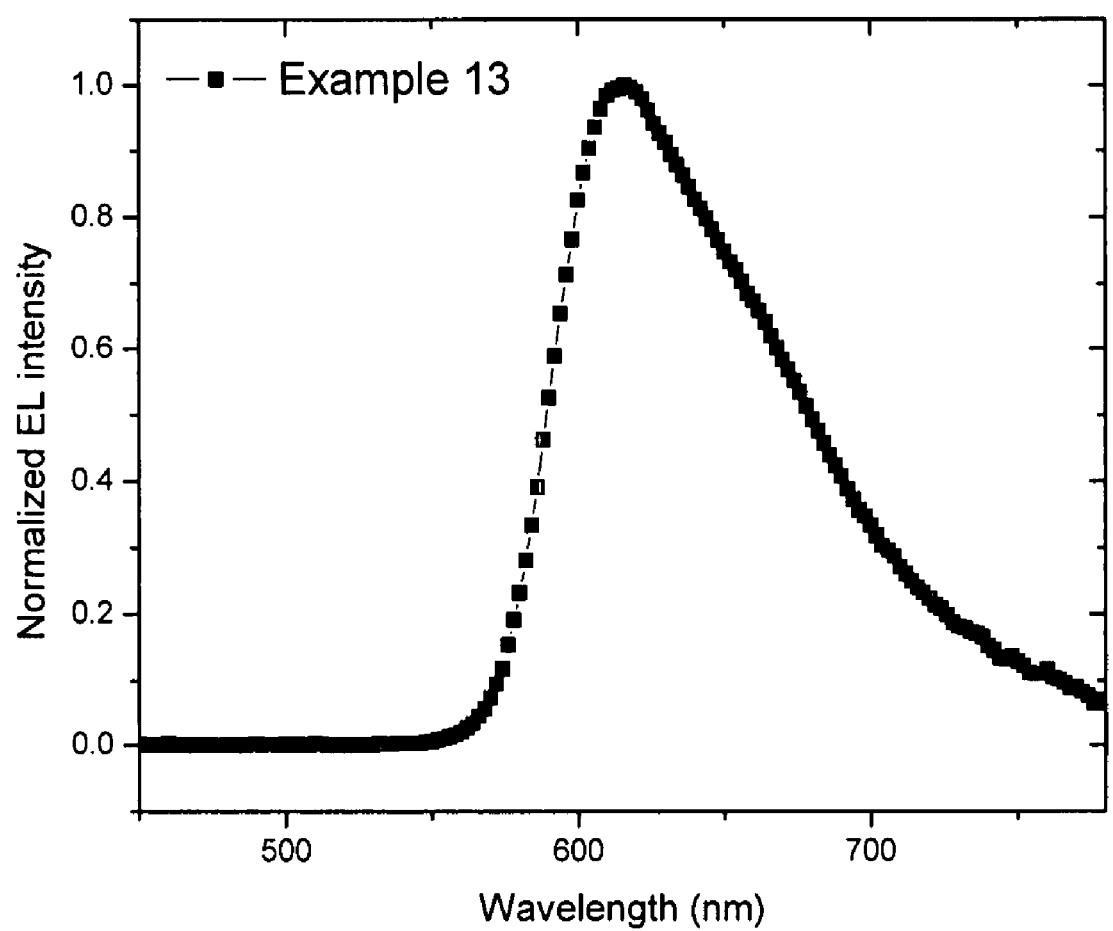
FIG. 16 shows the normalized electroluminescence spectra of example 13 using HPT as the ETL2.

FIG. 16 shows the normalized electroluminescence spectra of example 13 which utilize HPT as the ETL2.

Figure 17:
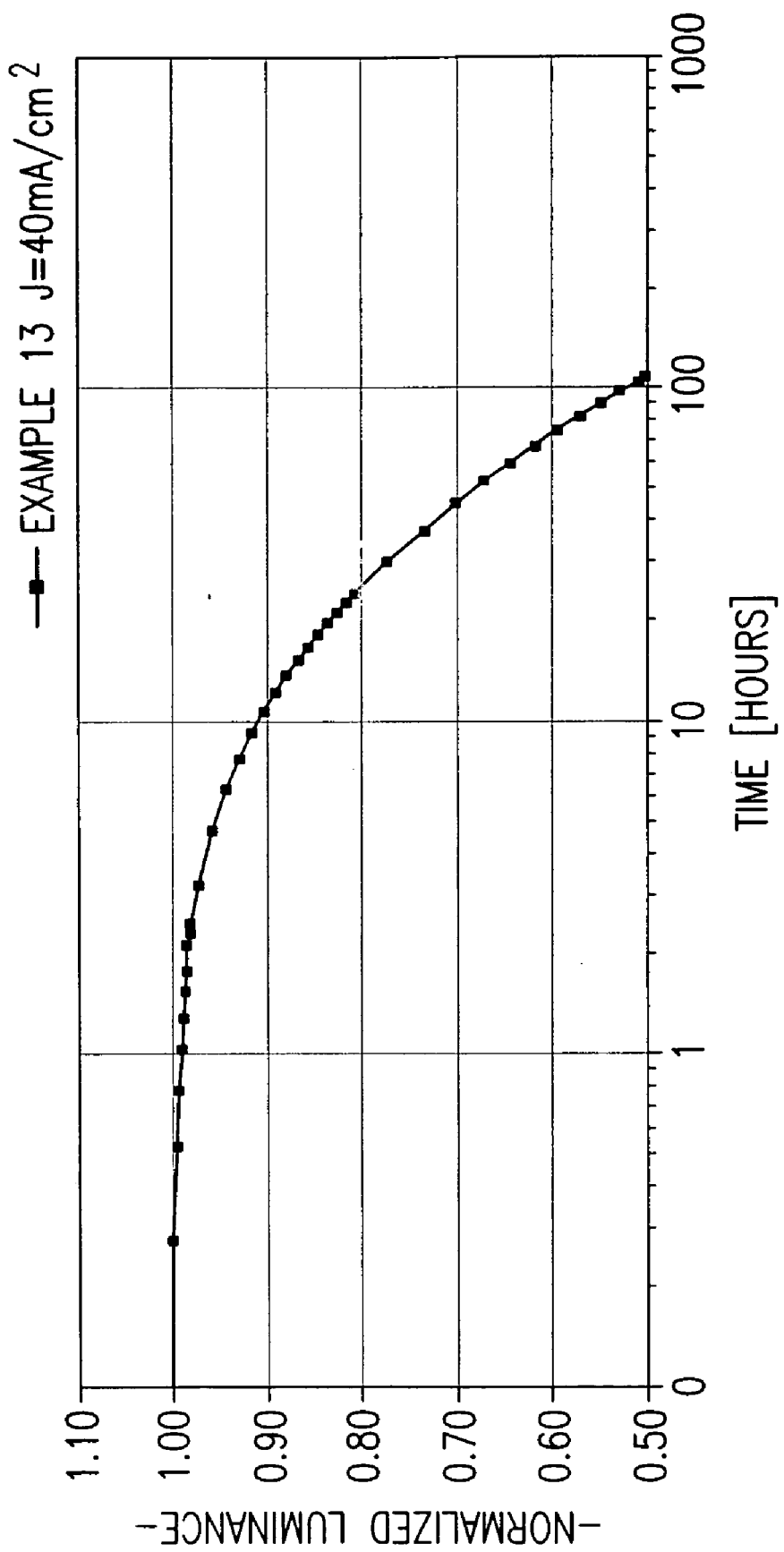
FIG. 17 shows operational stability for examples 13 using HPT as the ETL2 at room temperature under constant direct current of 40 mA/cm².

FIG. 17 shows the operational stability of examples 13 which utilize HPT as the ETL2 at room temperature under constant direct current of 40 mA/cm$^2$.

Figure 18:
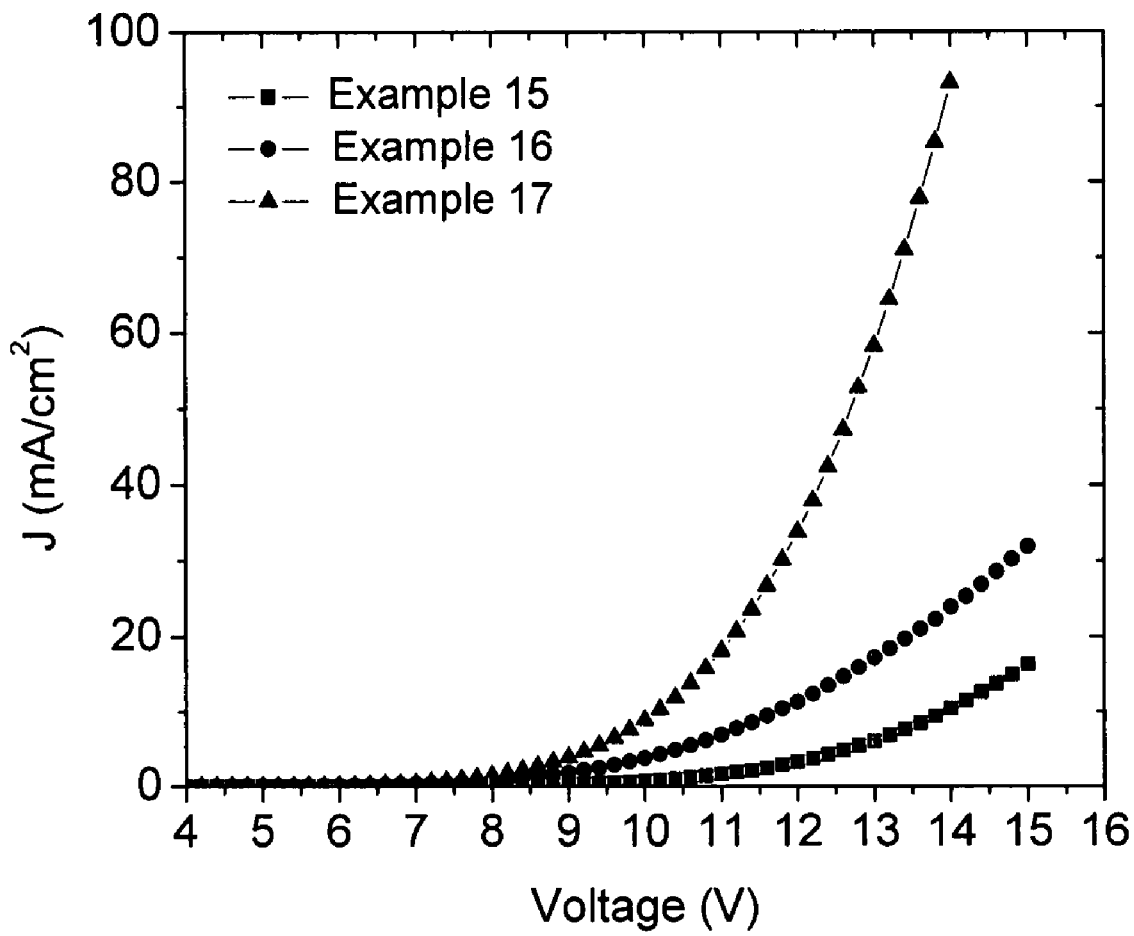
FIG. 18 shows the current-voltage characteristics for examples 15-17.

FIG. 18 shows the current-voltage characteristics of examples 15-17. Lowest voltage is required to operate example 17 which utilizes TSBF as the ETL2 and Alq as the ETL1. Highest voltage is required to operate example 15 which utilize TSBF as the ETL2 and there is no ETL1.

Figure 19:
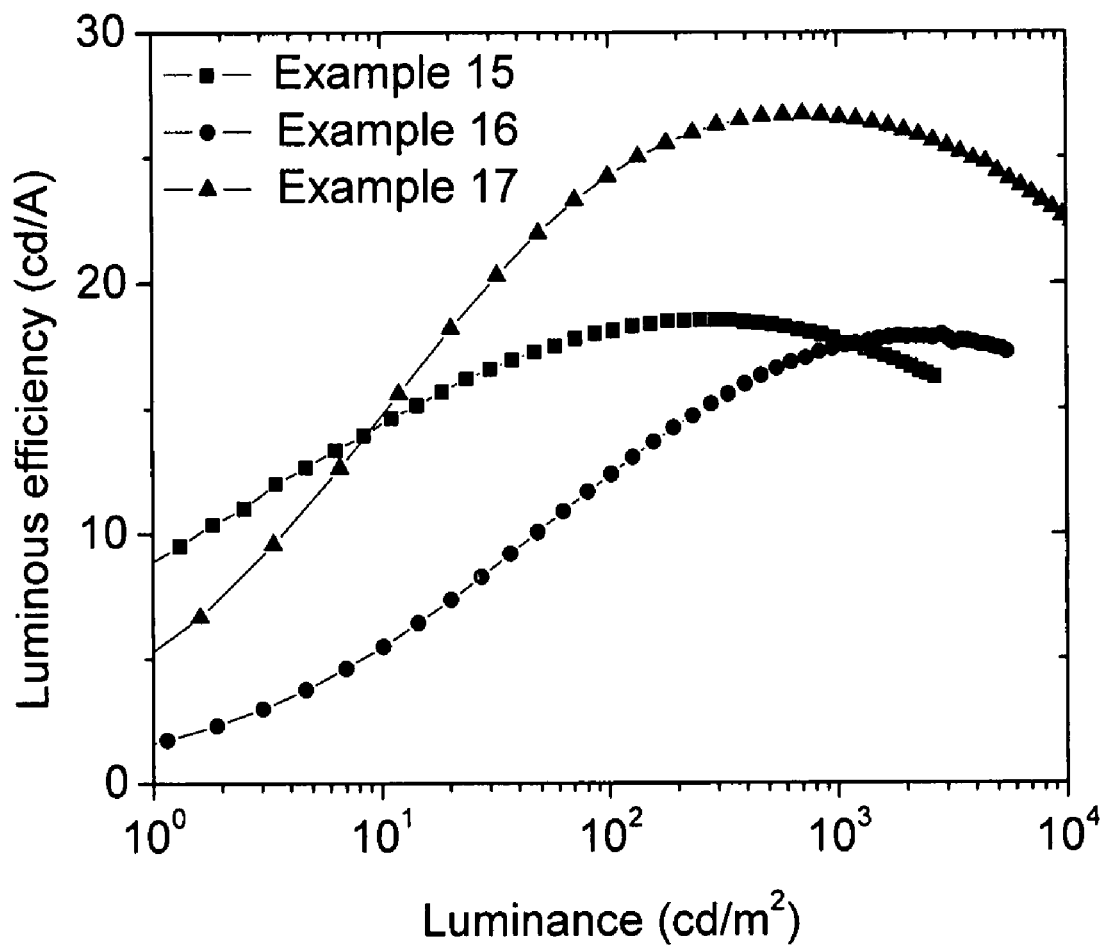
FIG. 19 shows luminous efficiency vs. brightness for examples 15-17.

FIG. 19 shows luminous efficiency vs. brightness for examples 15-17.

Figure 20:
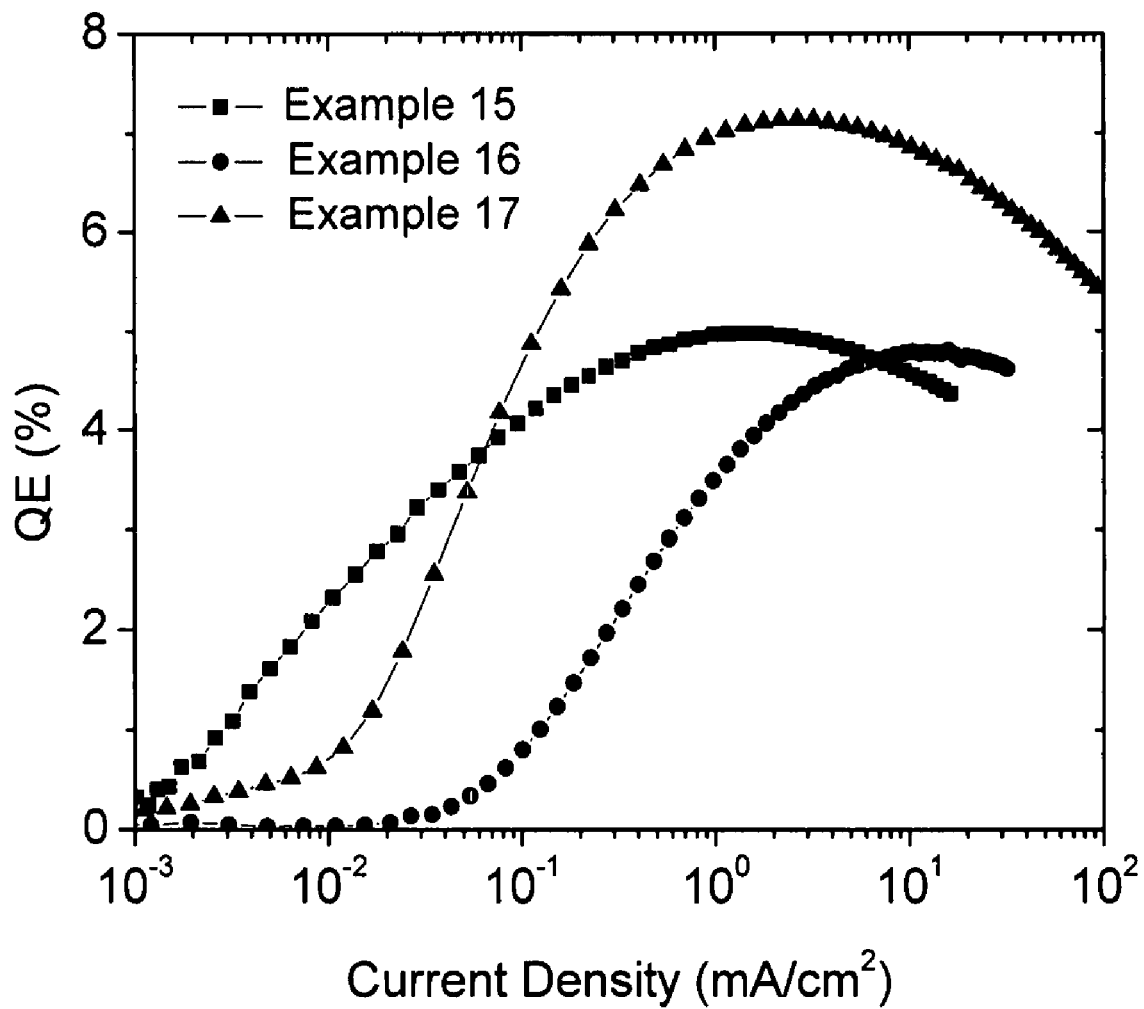
FIG. 20 shows external quantum efficiency vs. current density for examples 15-17.

FIG. 20 shows external quantum efficiency vs. current density for examples 15-17. Similar efficiency is obtained in example 17 which utilizes TSBF as the ETL2 compared to example 11 which utilizes BAlq as the ETL2.

Figure 21:
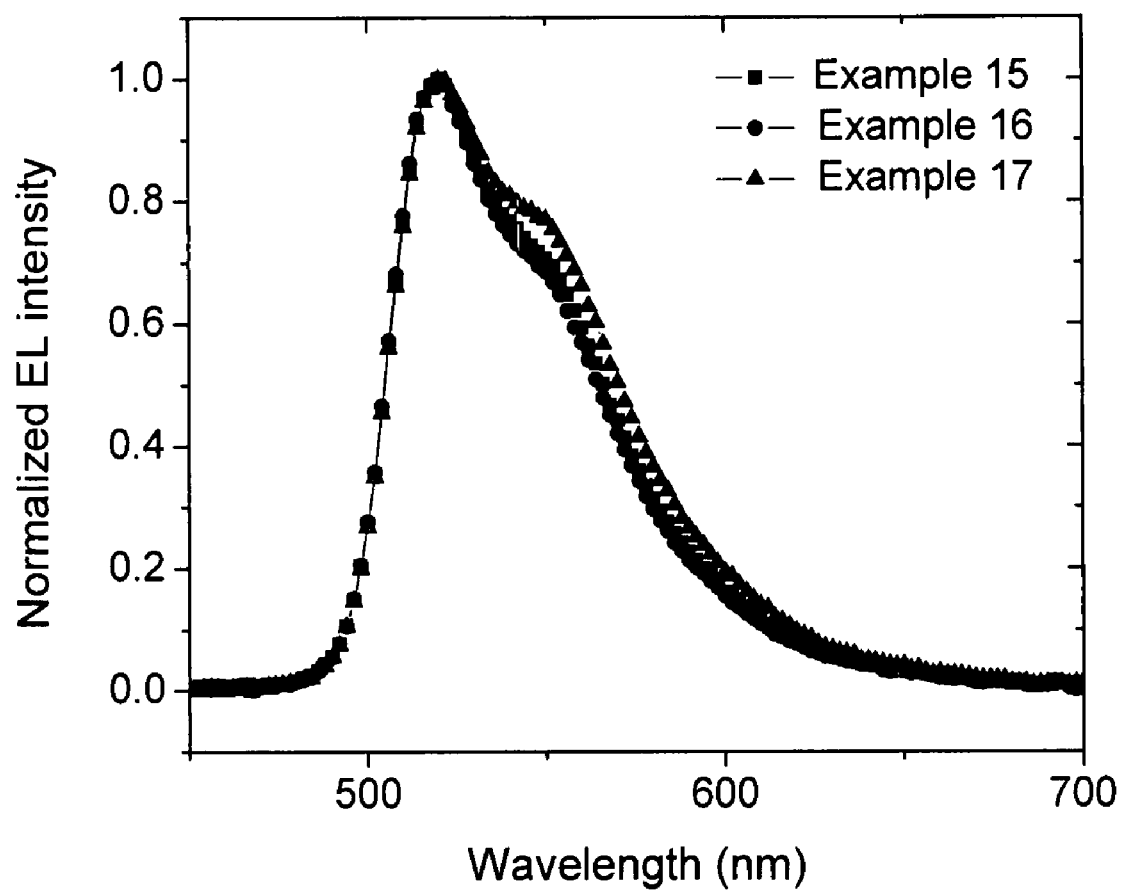
FIG. 21 shows the normalized electroluminescence spectra for example 15-17 using TSBF as the ETL2.

FIG. 21 shows the normalized electroluminescence spectra of examples 15-17 which utilize TSBF as the ETL2.

Figure 22:
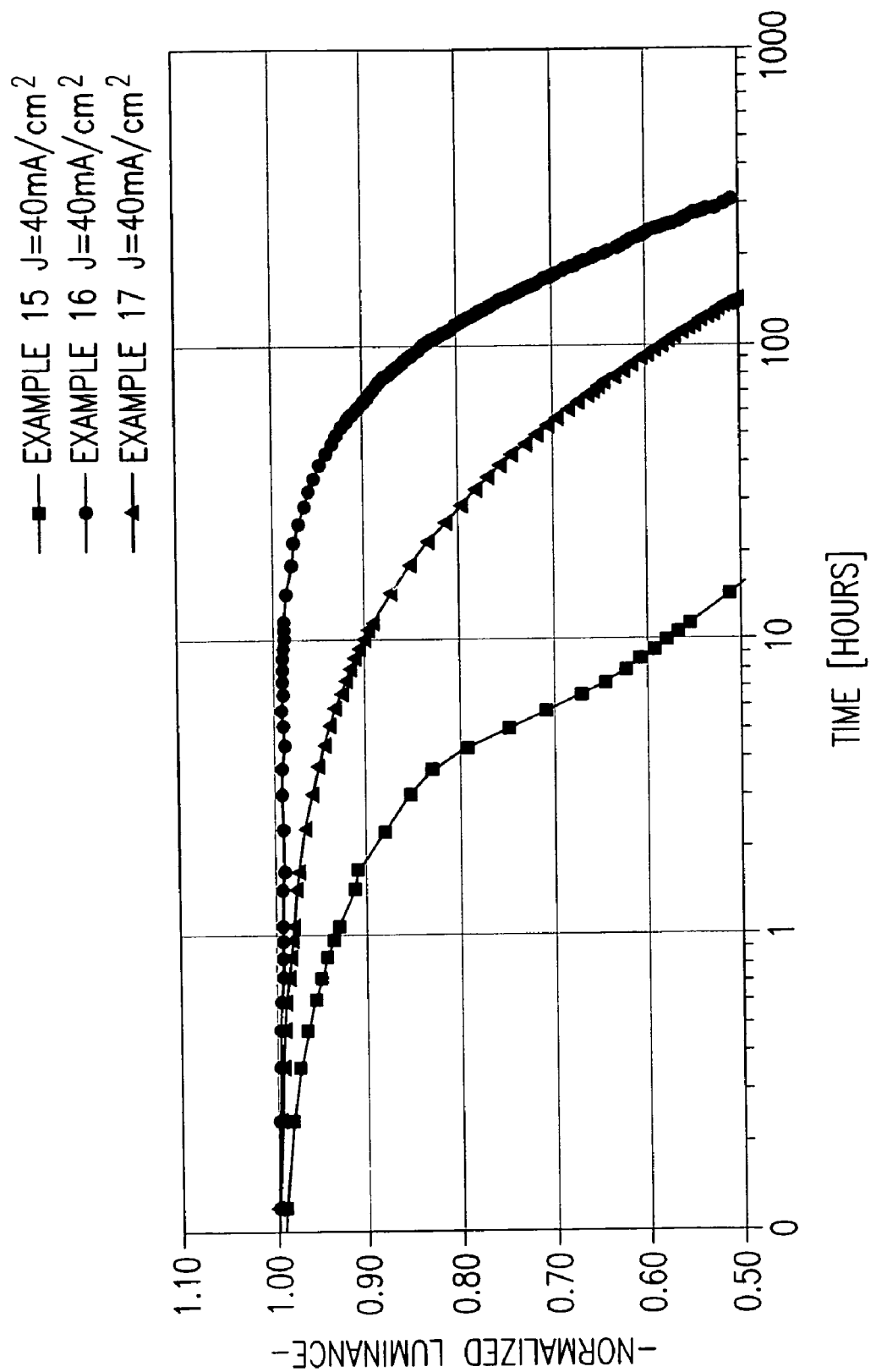
FIG. 22 shows the operational stability of examples 15-17 using TSBF as the ETL2 at room temperature under constant direct current of 40 mA/cm².

FIG. 22 shows the operational stability of examples 15-17 which utilizes TSBF as the ETL2 at room temperature under constant direct current of 40 mA/cm$^2$.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. A device, comprising:
    an anode;
    a cathode;
    a first organic layer disposed between the anode and the cathode, wherein the first organic layer comprises a material that produces phosphorescent emission when a voltage is applied between the anode and the cathode; and
    a second organic layer disposed between the first organic layer and the cathode, wherein the second organic layer comprises a compound having the structure:

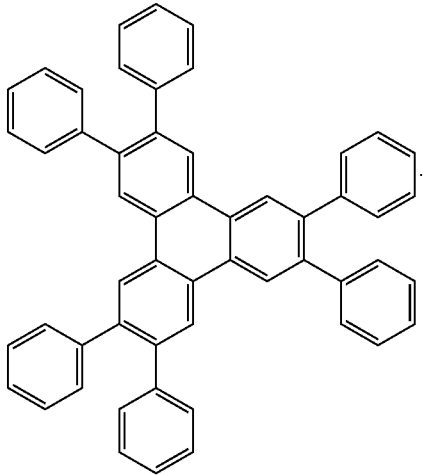

2. The device of claim 1, wherein the second organic layer is in direct contact with the cathode.

3. The device of claim 1, further comprising a third organic layer disposed between the second organic layer and the cathode.

4. The device of claim 3, wherein the second organic layer and the third organic layer are both electron transport layers, wherein the electron transport layers are different.

5. The device of claim 1, wherein the first organic layer further comprises a hole transporting material, and wherein the compound has a highest occupied molecular orbital that is not more than 0.81 eV less than the highest occupied molecular orbital of the hole transporting material in the first organic layer.

6. The device of claim 1, wherein after 100 hours of operation at room temperature with a constant direct current that produces an initial luminance of 600 cd/m$^2$, the device is capable of retaining at least about 90% of initial luminance.

7. The device of claim 1, wherein the second organic layer is in direct contact with the first organic layer.

8. The device of claim 7, wherein the second organic layer is a hole blocking layer.

9. The device of claim 1, wherein the second organic layer is an electron transport layer.

* * * * *